US010851151B2

(12) United States Patent
Kwon

(10) Patent No.: US 10,851,151 B2
(45) Date of Patent: Dec. 1, 2020

(54) EPITOPE FOR SWITCHING TO $T_H17$ CELL AND USE THEREOF

(71) Applicant: Eutilex Co., Ltd., Seoul (KR)

(72) Inventor: Byoung S. Kwon, Seoul (KR)

(73) Assignee: Eutilex Co., Ltd., Seoul (KR)

( * ) Notice: Subject to any disclaimer, the term of this patent is extended or adjusted under 35 U.S.C. 154(b) by 371 days.

(21) Appl. No.: 15/815,396

(22) Filed: Nov. 16, 2017

(65) Prior Publication Data

US 2018/0170997 A1 Jun. 21, 2018

Related U.S. Application Data

(60) Continuation of application No. 15/053,360, filed on Feb. 25, 2016, now abandoned, which is a division of application No. 13/861,619, filed on Apr. 12, 2013, now Pat. No. 9,309,321.

(30) Foreign Application Priority Data

Jun. 8, 2012 (KR) .................. 10-2012-0061791
Aug. 13, 2012 (KR) .................. 10-2012-0088646

(51) Int. Cl.

| C07K 16/28 | (2006.01) |
|---|---|
| C07K 14/705 | (2006.01) |
| C07K 16/30 | (2006.01) |
| C07K 7/06 | (2006.01) |
| C07K 14/715 | (2006.01) |
| A61K 39/00 | (2006.01) |

(52) U.S. Cl.
CPC .......... *C07K 14/70578* (2013.01); *C07K 7/06* (2013.01); *C07K 14/7151* (2013.01); *C07K 16/2878* (2013.01); *C07K 16/3061* (2013.01); *A61K 2039/505* (2013.01); *C07K 2317/21* (2013.01); *C07K 2317/34* (2013.01); *C07K 2317/55* (2013.01); *C07K 2317/74* (2013.01); *C07K 2317/75* (2013.01)

(58) Field of Classification Search
None
See application file for complete search history.

(56) References Cited

U.S. PATENT DOCUMENTS

| 6,794,132 | B2 | 9/2004 | Buechler et al. |
|---|---|---|---|
| 7,728,114 | B2 * | 6/2010 | Mach et al. ............. 530/388.15 |
| 7,812,135 | B2 | 10/2010 | Smith et al. |
| 9,255,151 | B2 | 2/2016 | Kwon |
| 9,255,152 | B2 | 2/2016 | Kwon |
| 9,309,321 | B2 | 4/2016 | Kwon |
| 2002/0187526 | A1 | 12/2002 | Ruben et al. |
| 2003/0091995 | A1 | 5/2003 | Buechler et al. |
| 2007/0098719 | A1 | 5/2007 | Smith et al. |
| 2014/0065152 | A1 | 3/2014 | Kwon |
| 2014/0072565 | A1 | 3/2014 | Kwon |
| 2014/0072566 | A1 | 3/2014 | Kwon |
| 2016/0024177 | A1 | 1/2016 | Kwon |
| 2016/0046691 | A1 | 2/2016 | Kwon |
| 2016/0244503 | A1 | 8/2016 | Kwon |

FOREIGN PATENT DOCUMENTS

| JP | 2008278814 A | 11/2008 |
|---|---|---|
| WO | WO-2011028683 A1 | 3/2011 |

OTHER PUBLICATIONS

Chatenoud et al., Current Tonics in Microbiology and Immunology. vol. 74, pp. 121-134 (1991). (Year: 1991).*
Norman et al., Transpl Int (1994) 7:356-361. (Year: 1994).*
Graeber et al., Inflamm. Res. (2012) 61:87-96. (Year: 2012).*
Wen et al., Cancer Immunol Immunother (2008) 57:1781-1794. (Year: 2008).*
Deputy Commissioner for Patent Examination Policy, Robert W. Bahr, Memorandum of Feb. 22, 2018, 2 pages. (Year: 2018).*
Harlow et al. (Antibodies, a Laboratory Manual, Cold Spring Harbor laboratory, 1988, pp. 37-47). (Year: 1988).*
Edwards et al. (J. Mol. Biol. (2003) 334, 103-118) (Year: 2003).*
Lloyd et al. (Protein Engineering, Design & Selection vol. 22 No. 3 pp. 159-168, 2009). (Year: 2009).*
Meyer et al. (British Journal of Haematology, 2018, 180, 808-820). (Year: 2018).*
Wack et al. (Current Opinion in Virology 2011, 1:184-195). (Year: 2011).*
Khader et al. (Mucosal Immunol. Sep. 2009;2(5):403-11). (Year: 2009).*
McDonald DR (J Allergy Clin Immunol. Jun. 2012). (Year: 2012).*
Bae, E. et al., Glucocorticoid-induced tumour necrosis factor receptor-related protein-mediated macrophage stimulation may induce cellular adhesion and cytokine expression in rheumatoid arthritis, Clinical and Experimental Immunology, 148: 410-418 (2007).
Barbas et al., Methods: A Companion to Methods in Enzymology, 2: 119 (1991).
Chattopadhyay, K. et al., Evolution of GITRL immune function: murine GITRL exhibits unique structural and biochemical properties within the TNF superfamily, PNAS, 105(2): 635-640 (2008).
Dolff, S. et al., Disturbed Th1, Th2, Th17 and Treg balance in patients with systemic lupus erythematosus, Clin Immunol., 141(2): 197-204 (2011).

(Continued)

*Primary Examiner* — Zachary S Skelding
(74) *Attorney, Agent, or Firm* — Fish & Richardson P.C.

(57) ABSTRACT

The present invention relates to a novel epitope to convert T cell to type 17 helper T ($T_H17$) cell. Specifically, the present invention relates to an epitope constituting the 41st to 50th amino acids (SEQ ID No.2) of extracellular domain (ECD) of activation-inducible tumor necrosis factor receptor (AITR), an antibody recognizing the epitope, a polynucleotide encoding the epitope, a polynucleotide encoding the antibody, an expression vector comprising the polynucleotide encoding the epitope or antibody, a transformant introduced with the vector, a composition comprising the antibody for converting T cell to $T_H17$ cell and a method of conversion for the same, a pharmaceutical composition comprising the antibody for preventing or treating infectious disease, a method for treating infectious disease using the antibody, a composition comprising the antibody for enhancing immunity, and a method for enhancing immunity using the antibody.

17 Claims, 19 Drawing Sheets

Specification includes a Sequence Listing.

(56) References Cited

OTHER PUBLICATIONS

Fawcett, J. et al., Mapping the homotypic binding sites in CD31 and the role of CD31 adhesion in the formation of interendothelial cell contacts, J Cell Biol., 128(6): 1229-1241 (1995).
Gurney, A.L., et al., Identification of a new member of the tumor necrosis factor family and its receptor, a human ortholog of mouse GITR, Current Biology, 9(4):215-218 (1999).
Ha, H., TRAF-Mediated TNFR-Family Signaling, Curr Protoc Immunol., Chapter II: Unit 11.9D.1-11.9D.19 (Nov. 2009).
Hanabuchi, S. et al., Human plasmacytoid predendritic cells activate NK cells through glucocorticoid-induced tumor necrosis factor receptor-ligand (GITRL), Blood,107: 3617-3623 (2006).
Harlow et al. (Using Antibodies: a Laboratory Manual, Cold Spring Harbor Laboratory Press, 1999, p. 4).
Hermann-Kleiter, N. and Baier, G., NFAT pulls the strings during CD4+ T helper cell effector functions, Blood, 15: 2989-2997 (2010).
Horn, I.R. et al., Selection of phage-displayed Fab antibodies on the active conformation of Ras yields a high affinity conformation-specific antibody preventing the binding of c-Raf kinase to Ras, FEBS Letters, 463: 115-120 (1999).
Ikeda H, et al., The roles of IFN gamma in protection against tumor development and cancer immunoediting, Cytokine Growth Factor Rev., 13(2), 95-109 (2002).
Kim et al., Korean J Otorhinolaryngology-Head Neck Surg, 53(12): 737-748 (2010).
Kwon, B. et al., Identification of a novel activation-inducible protein of the tumor necrosis factor receptor superfamily and its ligand, J. Biol. Chem., 274(10): 6056-6061 (1999).
Kwon, Byoung Se, "The 2012 Spring Conference of the Korean Association of Immunology," English Abstract and Presentation Program presented at Seoul Kyoyuk Munhwa Hoekwar, pp. 1-5, Apr. 12-13, 2012.
Liu Z et al., Tumor regulatory T cells potently abrogate antitumor immunity, J.Immunol., 182(10): 6160-7 (2009).
Malian, F., NFAT proteins: key regulators of T-cell development and function, Nat Rev Immunol., 5(6): 472-484 (2005).
Memorandum from Andrew H. Hirshfeld, Deputy Commissioner for Patent Examination Policy, United States Patent and Trademark Office, 19 pages (Mar. 4, 2014).
Recombinant DNA, Wikipedia, pp. 1-9 (dated May 8, 2012). URL: https://web.archive.org/web/20120508143225/http://en.wikipedia.org/wiki/Recombinant_DNA [Retrieved Jan. 8, 2018].
Rodríguez-Reyna, T.S. et al., Th17 peripheral cells are increased in diffuse cutaneous systemic sclerosis compared with limited illness: a cross-sectional study, Rheumatol Int., 32:2653-2660 (2012).
Stockinger, B. and Veldhoen, M., Differentiation and function of Th17 T cells., Curr Opin Immunol., 19(3): 281-286 (2007).
Truchetet, M-E et al., Increased frequency of circulating Th22 in addition to Th17 and Th2 lymphocytes in systemic sclerosis: association with interstitial lung disease, Arthritis Research & Therapy, 13: R166 (2011).
United States Patent and Trademark Office Department of Commerce, 2014 Interim Guidance on Subject Matter Eligibility (2014 IEG), pp. 1-44 (issued Dec. 16, 2014).
United States Patent and Trademark Office Department of Commerce, Subject Matter Eligibility Examples: Life Sciences, 2014 Interim Guidance on Subject Matter Eligibility (2014 IEG), pp. 1-31 (May 2016).
United States Patent and Trademark Office Department of Commerce, Evaluating subject Matter Eligibility Under 35 U.S.C. § 101, pp. 1-93 (updated Mar. 19, 2014).
Winter, G. et al., Making antibodies by phage display technology, Ann. Rev.Immunol., 12: 433-455 (1994).
Zhu, J. and Paul, W.E., CD4 T cells: fates, functions, and faults, Blood, 112: 1557-1569 (2008).
Zwick, M. B. et al., Identification and Characterization of a Peptide That Specifically Binds the Human, Broadly Neutralizing Anti-Human Immunodeficiency Virus Type 1 Antibody b12, J. Virol., 75(14): 6692-6699 (2001).
Kohler and Milstein, "Continuous cultures of fused cells secreting antibody of predefined specificity", Nature, 256: 495-497, 1976.

\* cited by examiner

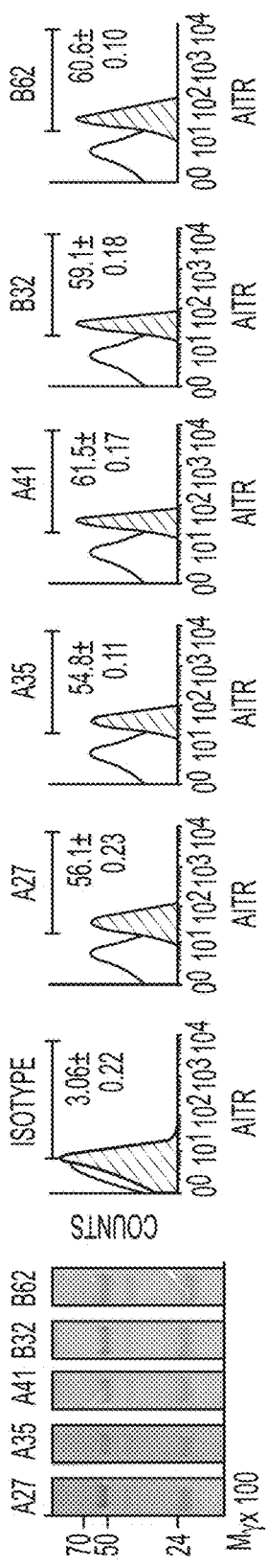
FIG. 1A
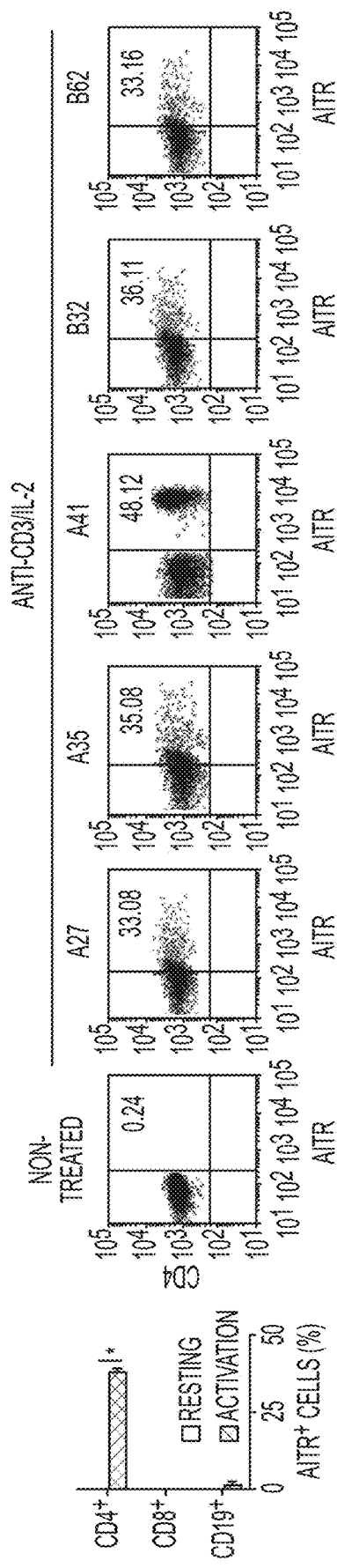
FIG. 1B
FIG. 1C
FIG. 1D

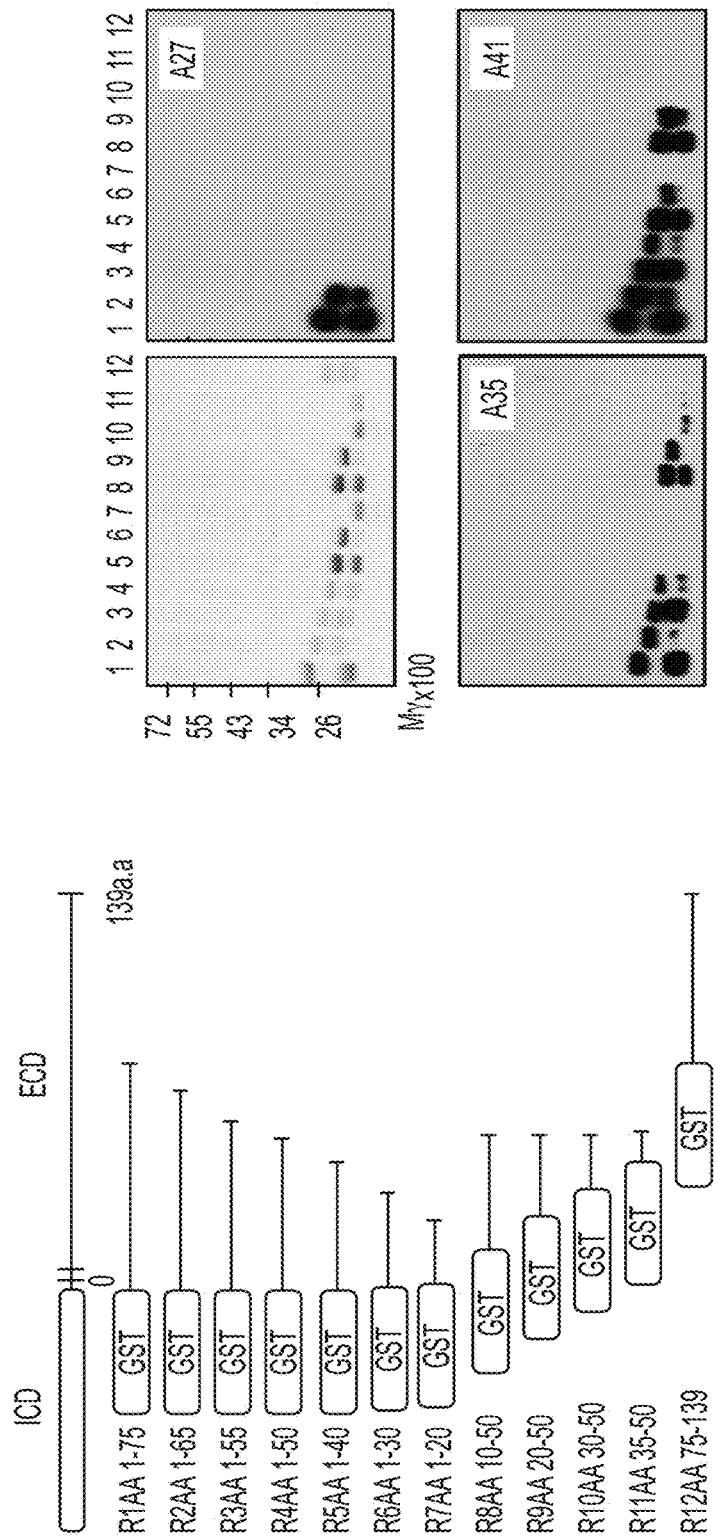

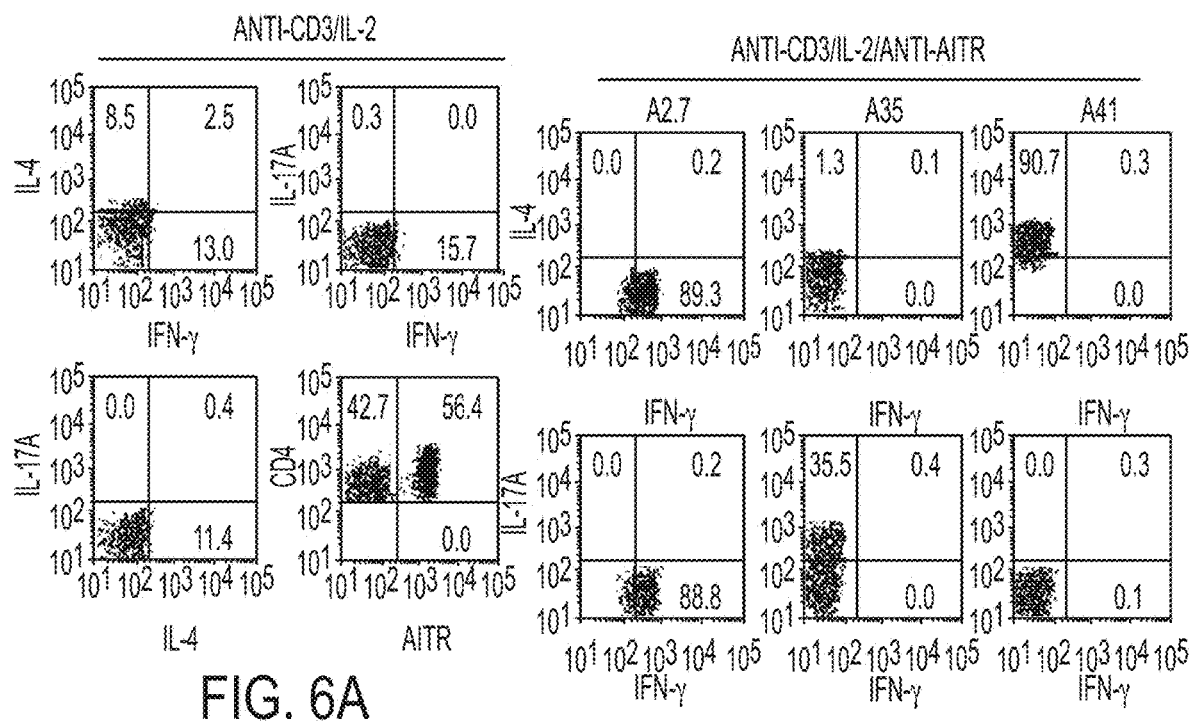
FIG. 6A
FIG. 6B
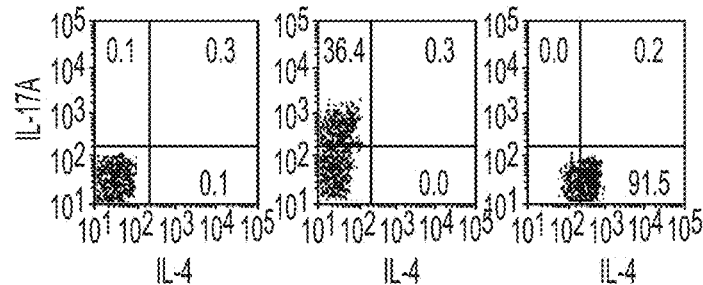
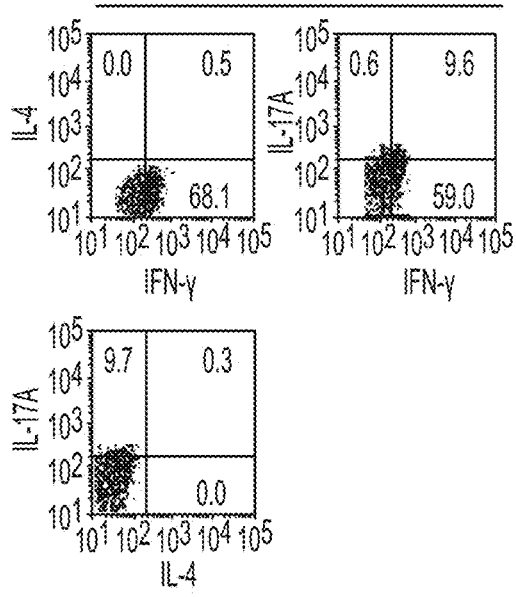
FIG. 6C

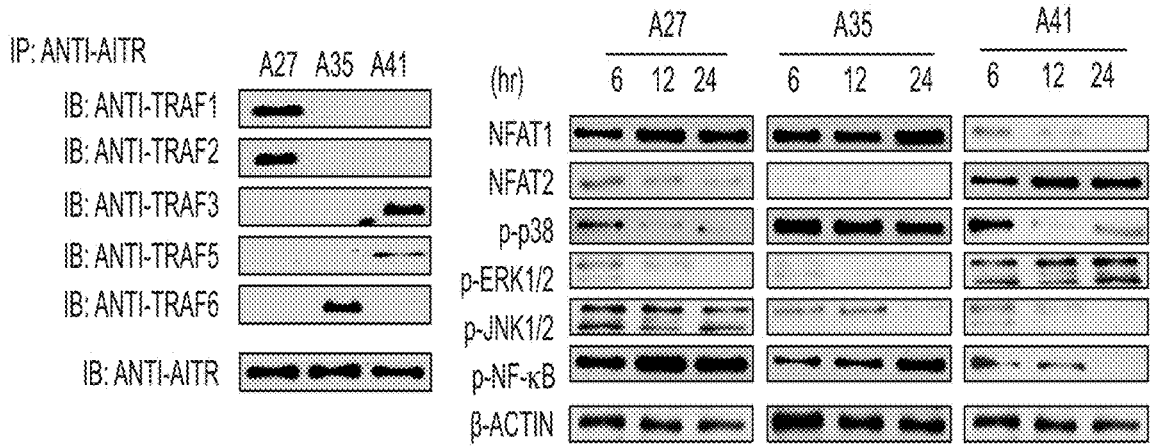
FIG. 7A
FIG. 7B
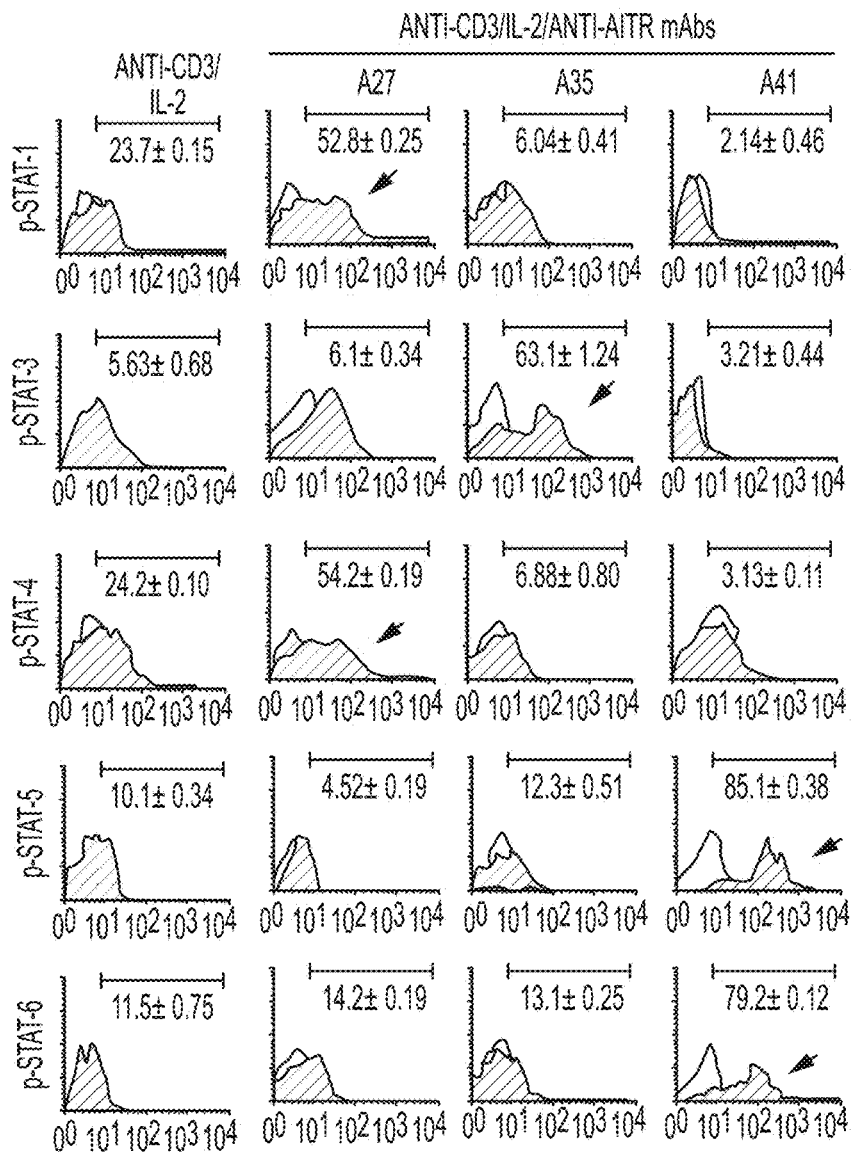
FIG. 7C

| SIGNALING TRANSDUCTION MOLECULES | A27 | A35 | A41 |
|---|---|---|---|
| HUMAN CD4$^+$ T CELLS | | | |
| TRAF1 | +++ (VIA TRAF2) | - | - |
| TRAF2 | +++ | - | - |
| TRAF3 | - | - | +++ |
| TRAF5 | - | - | + |
| TRAF6 | - | +++ | - |
| NFAT1 | +++ | +++ | - |
| NFAT2 | + | - | +++ |
| p38 | + | +++ | + |
| ERK1/2 | - | - | ++ |
| JNK1/2 | ++ | + (JNK1) | - |
| NF-κB | +++ | ++ | + |
| HUMAN T$_{REG}$ CELLS | | | |
| TRAF1 | +++ (VIA TRAF2) | - | - |
| TRAF2 | ++ | - | - |
| TRAF3 | - | - | ++ |
| TRAF5 | - | - | +++ |
| TRAF6 | - | + | - |
| NFAT1 | +++ | +++ | +++ |
| NFAT2 | + | - | - |
| p38 | + | +++ | - |
| ERK1/2 | - | - | +++ |
| JNK1/2 | + | + (JNK1) | - |
| NF-κB | +++ | + | ++ |

ASSOCIATION LISTED INCLUDE ONLY THOSE VERIFIED TO OCCUR BETWEEN ENDOGENOUS TRAFs AND DOWNSTREAM SIGNALING TRANSDUCTION MOLECULES AND AITR IN CD4$^+$ T CELLS AND T$_{REG}$ CELLS.
+++ = STRONG SIGNALS; ++ = MIDDLE SIGNAL; + = WEAKER BUT REPRODUCIBLY DETECTABLE SIGNALS; - = NO SIGNALS DETECTED BY IMMUNOBLOTTING EXPERIMENTS

FIG. 8

| SIGNALING TRANSDUCTION MOLECULES | A27 | A35 | A41 |
|---|---|---|---|
| HUMAN CD4⁺ T CELLS | | | |
| STAT1 | +++ | - | - |
| STAT3 | - | +++ | - |
| STAT4 | +++ | - | - |
| STAT5 | - | - | +++ |
| STAT6 | - | - | +++ |
| T-BET | ↑ | ↓ | ↓ |
| GATA-3 | ↓ | ↓ | ↑ |
| RORγt | ↓ | ↑ | ↓ |
| Foxp3 | NO | NO | NO |
| HUMAN T$_{REG}$ CELLS | | | |
| STAT1 | +++ | - | - |
| STAT3 | - | +++ | - |
| STAT4 | +++ | - | - |
| STAT5 | - | - | +++ |
| STAT6 | - | - | + |
| T-BET | ↑ | ↓ | ↓ |
| GATA-3 | ↓ | ↓ | ↓ |
| RORγt | ↓ | ↑ | ↓ |
| Foxp3 | ↓ | ↓ | ↑ |

ASSOCIATION LISTED INCLUDE ONLY THOSE VERIFIED TO OCCUR BETWEEN ENDOGENOUS STATs AND MASTER TRANSCRIPTION FACTORS IN CD4⁺T CELLS AND T$_{REG}$CELLS. +++ = STRONG SIGNALS; ++ = MIDDLE SIGNAL; + = WEAKER BUT REPRODUCIBLY DETECTABLE SIGNALS; - = NO SIGNALS DETECTED BY FACS CYTOMETRY EXPERIMENTS

FIG. 9

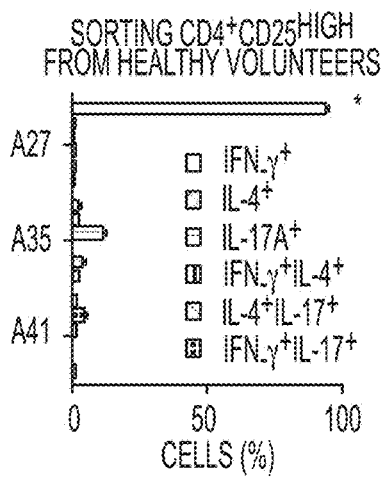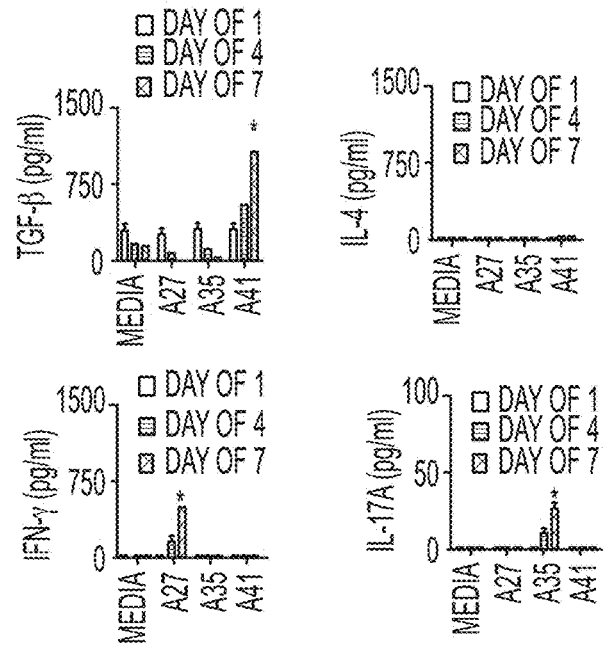
FIG. 12A
FIG. 12B
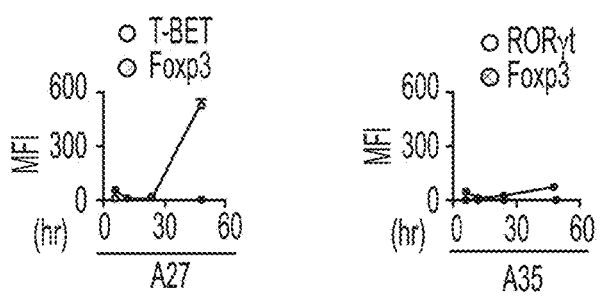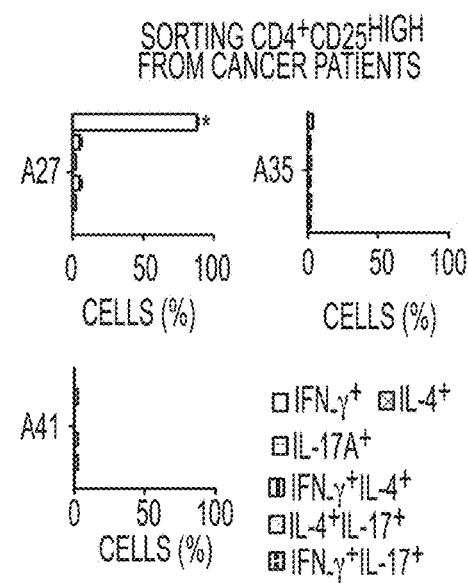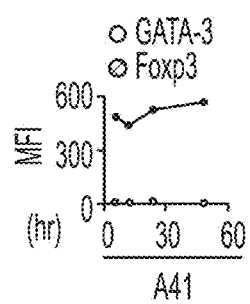
FIG. 12C
FIG. 12D

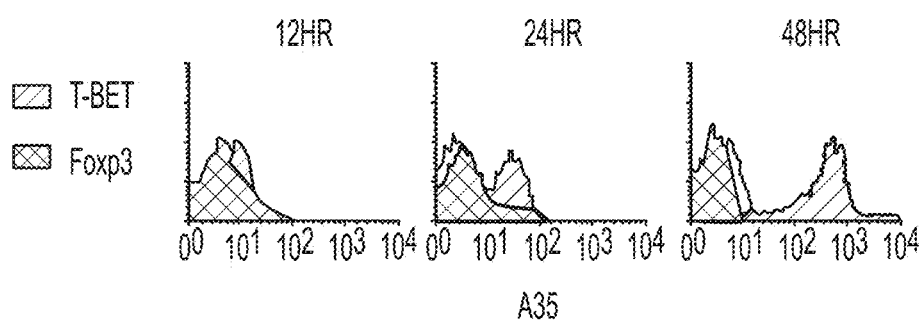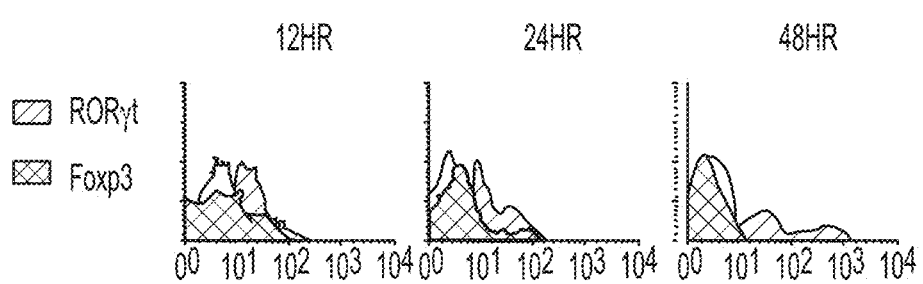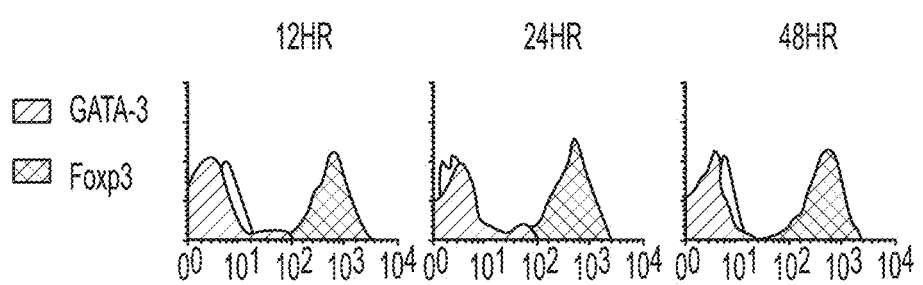
FIG. 15B

EPITOPE FOR SWITCHING TO $T_H17$ CELL AND USE THEREOF

CROSS-REFERENCE TO RELATED PATENT APPLICATIONS

This patent application is a continuation of U.S. patent application Ser. No. 15/053,360, filed on Feb. 25, 2016, which is a divisional of U.S. patent application Ser. No. 13/861,619, filed Apr. 12, 2013, which claims priority from Korean Application No. 10-2012-0061791 filed on Jun. 8, 2012, and Korean Application No. 10-2012-0088646 filed on Aug. 13, 2012, all of which are incorporated herein by reference in their entireties.

TECHNICAL FIELD

The present invention relates to a novel epitope to convert T cell to type 17 helper T ($T_H17$) cell. Specifically, the present invention relates to an epitope constituting the 41st to 50th amino acids (SEQ ID No.2) of extracellular domain (ECD) of activation-inducible tumor necrosis factor receptor (AITR), an antibody recognizing the epitope, a polynucleotide encoding the epitope, a polynucleotide encoding the antibody, an expression vector comprising the polynucleotide encoding the epitope or antibody, a transformant introduced with the vector, a composition comprising the antibody for converting T cell to $T_H17$ cell and a method of conversion for the same, a pharmaceutical composition comprising the antibody for preventing or treating infectious disease, a method for treating infectious disease using the antibody, a composition comprising the antibody for enhancing immunity, and a method for enhancing immunity using the antibody.

BACKGROUND ART

Various types of receptors belonging to the tumor necrosis factor receptor superfamily (TNFR) superfamily are involved in the regulation of cell proliferation, cell differentiation, and cell death. Also, TNFR receptors play an important role in development of immune response, tumor necrosis, and protection against autoimmune diseases. Examples of the TNFR receptors include CD28, 4-1BB, OX40, CD40, or CD27.

Human activation-inducible tumor necrosis factor receptor (AITR) is a member of TNFR superfamily, and is also called glucocorticoid-induced TNFR-related protein (GITR), tumor necrosis factor receptor superfamily member 18 (TNFRSF18), or CD357. AITR is a type I transmembrane protein of TNFR superfamily. Immunoregulatory T cell ($T_{reg}$ cell or CD4$^+$CD25$^{high}$ T cell) constitutively expresses GITR at high level, and when peripheral blood mononuclear cell (PBMC) is activated, expression of GITR is rapidly up-regulated. In particular, a signal transduction through GITR is known to inhibit a suppressive function of $T_{reg}$ cells, which in turn increase a resistance of CD4$^+$ and CD8$^+$ T cells to the suppression by $T_{reg}$ cells, thereby activating the CD4$^+$ and CD8$^+$ T cells. Also, a monoclonal antibody (mAb, e.g., DTA-1) that specifically binds to GITR or a physiological ligand thereof i.e., GITRL is known to enhance antitumor immunity through various in vivo models. On the other hand, activation of GITR inhibits $T_{reg}$ cell which is capable of suppressing the autoreactive T cells, thereby promoting autoimmune response.

Although there has not been much information found about the biological functions of AITR and AITR ligand (AITRL), it is known that AITR is expressed at basal level in a resting T cell, but its expression level rapidly increases upon activation of T cell. Also, it has been reported that AITR expression level was increased in herniated disc tissue cell isolated from lumber disc herniation patients as well as in the $T_{reg}$ cells from active systemic lupus erythematosus patients.

AITR binds with TNFR-associated factors (TRAFs) such as TRAF1, TRAF2 and TRAF3. When AITR interacts with its ligand, this recruits TRAF2 and ultimately activates NF-KB/NIK (Kwon, B. et al., J Biol Chem 274, 6056-6061, 1999). TRAF protein is a type of cytoplasmic adapter protein, and is involved in signal transduction for extracellular proliferation, differentiation, activation and migration. The N-terminal sites of TRAF proteins vary a lot, and all of the TRAF proteins except for TRAF1 possess a RING-finger motif at the N-terminal site thereof. A RING-finger is essential for the TRAF-mediated signal transduction. In the previous study, when the genes encoding all six types of TRAF proteins were knockout in mouse by gene targeting, various phenotypes were observed, suggesting that TRAFs have significantly various biological functions (Ha, H., Curr Protoc Immunol. Chapter 11:Unit11.9D, 2009).

A Ca$^{2+}$-dependent transcription factor known as nuclear factor of activated T cells (NFATs) regulates not only T cells but also various types of growth factors and cytokines. Also, it regulates cell-to-cell interaction molecules essential for morphogenesis, development, and other functions in various types of cells and organs. Recently, NFAT is shown to be an important factor in induction of specific genetic programs that regulate differentiation to $T_H$ lineage and effector or regulatory functions of $T_H$ cells, via the transcriptional regulation of $T_H$ lineage-specific transcription factors such as T-bet ($T_H1$), GATA-3 ($T_H2$), RORγt ($T_H17$), and Foxp3 ($T_{reg}$). In addition, it has been reported that NFAT family regulates transcription of various cytokines and cytokine receptors thereof (Macian, F. Nat Rev Immunol. 5, 472-484, 2005).

One of the most important factors determining the fate of CD4$^+$ T cell is cytokine milieu during the TCR-mediated activation of naive CD4$^+$ T cell. The major signaling pathway triggered by cytokines is an activation of the signaling transducer proteins and activator of transcription (STAT) family. The STAT proteins play an essential role in differentiation and expansion of $T_H$ cells. In particular, IFN-γ/NFAT1/STAT-1 pathway activates T-bet which is the master transcription factor specifying the lineage, while NFAT1/STAT-3 pathway activates RORγ which is the master transcription factor specifying the $T_H17$ lineage. Also, IL-4/NFAT2/STAT-6 pathway activates GATA-3 which is the master transcription factor specifying the lineage, and NFAT1/STAT-5 pathway activates Foxp3 which is the master transcription factor specifying the $T_{reg}$ lineage. These complex intracellular signaling cascades play an important role in determining the differentiation of $T_H$ cell and functions thereof.

Naive CD4 T cell can differentiate into four different types of T cells such as $T_H1$, $T_H2$, $T_H17$, and induced $T_{reg}$ cells. Each of the T cells has different function and among them, IL-17A-secreting $T_H17$ cell is involved in inducing immune response against extracellular bacteria and fungus. Cytokines secreted by $T_H17$ cell include IL-17A, IL-17F, IL-21, and IL-22, and among them IL-17A is especially well known. IL-17A which is a representative cytokine secreted by $T_H17$ cell promotes the translocation and de novo production of neutrophils through granulocyte-colony stimulating factor (G-CSF). IL-17A is also takes an important role in host defense against extracellular bacteria such as *Klebsiella pneumonia* (Brigitta Stockinger and Marc Veldhoen, Curr Opin Immunol. 19(3):281-6; 2007)

As $T_H17$ cells induce immune response to infectious disease caused by microorganisms such as bacteria and fungus, thereby taking an important role in treatment of infectious disease. Therefore, identifying a substance that can induce cell differentiation to $T_H17$ cell is important in the development of therapeutic method for treating infectious disease. Also, $T_H17$ cell secrets a cytokine like IL-17A promoting the immune response, and thus finding the substance that can promote cell differentiation to $T_H17$ cell can help identifying the substance that can enhance immune response.

DISCLOSURE

Technical Problem

In effort to investigate a method for differentiating T cell specifically to $T_H17$ cell, the present inventors have confirmed that AITR-specific antibody, which binds specifically to a sequence of 41st to 50th amino acids of AITR-ECD in a regulatory T cell, can convert T cell specifically to $T_H17$ cell, thereby completing the present invention.

Technical Solution

One object of the present invention is to provide a polypeptide which is an epitope, represented by an amino acid sequence of SEQ ID No.2, of activation-inducible tumor necrosis factor receptor (AITR) for converting T cells to type 17 helper T cell ($T_H17$) cell.

Another object of the present invention is to provide an antibody specifically recognizing the epitope of AITR, represented by SEQ ID No.2.

Another object of the present invention is to provide a method for preparing the antibody.

Another object of the present invention is to provide a polynucleotide encoding the epitope or antibody, an expression vector comprising the polynucleotide, and a transformant introduced with the vector.

Another object of the present invention is to provide a composition comprising the antibody for converting T cell $T_H17$ cell.

Another object of the present invention is to provide a method for converting T cell to $T_H17$ cell, comprising the step of treating T cell with the antibody.

Another object of the present invention is to provide a pharmaceutical composition comprising the antibody for preventing or treating infectious diseases.

Another object of the present invention is to provide a method for treating infectious diseases using the antibody.

Another object of the present invention is to provide a composition comprising the antibody, for enhancing immunity.

Another object of the present invention is to provide a method for enhancing immunity by using the antibody.

Advantageous Effects

The present invention has identified a new epitope of AITR, represented by SEQ ID No.2, which can convert T cell to $T_H17$ cell. Also, it was confirmed that an antibody that can specifically recognize the epitope can effectively convert T cell to $T_H17$ cell. Accordingly, the newly identified epitope of the present invention for converting to $T_H17$ cells can be used for treatment of various diseases or research purpose that needs $T_H17$ cells. Furthermore, the antibody of the present invention effectively converts T cells to $T_H17$ cells. Therefore, the antibody can be effectively used for preventing or treating a disease like infectious disease which requires increased number of $T_H17$ cells.

DESCRIPTION OF DRAWINGS

FIG. 1A shows the Coomassie blue-stained gel showing the presence of anti-AITR Fab clones selected by phage displaying; and bivalent forms of anti-AITR mAbs that were generated from transiently transfected HEK293. FIG. 1B shows flow cytometry analysis results demonstrating the binding of anti-AITR mAbs to AITR in AITR-overexpressed Jurkat cells that were stained with PE-conjugated anti-AITR mAbs. FIG. 1C shows the proportion of AITR-expressing cells (%) in a population of CD4$^+$, CD8+, and CD19$^+$ cells. PBMCs were stimulated with anti-CD3/IL-2 or lipopolysaccharide (LPS) for 2 days and stained with PE-conjugated anti-AITR mAb (clone A41) FIG. 1D shows the expression of AITR in activated CD4$^+$ T cells. The purified CD4$^+$ T cells were stimulated with anti-CD3/IL-2 for 3 days. AITR expression in the activated CD4$^+$ T cells was detected with PE-conjugated anti-AITR mAbs. Together, FIG. 1A-D illustrate the process of generating anti-AITR mAbs from a human antibody library.

FIG. 2A and FIG. 2B show the expression of AITR in CD4$^+$ T cells in an activation-dependent manner. Isolated PBMCs were stimulated with anti-CD3/IL-2 or LPS for 2 days.

FIG. 3A shows a schematic diagram of full-length AITR and recombinant GST protein lysates used for antibody production and epitope mapping. Top: an intracellular domain (ICD) and an extracellular domain (ECD) of AITR. Bottom: twelve AITR recombinants R1, R2, and R3 to R12 (R3-R12). FIG. 3B shows western blotting analysis demonstrating a specific binding of anti-AITR mAbs to each fragment of AITR-ECD. Fragments of AITR-GST proteins are shown by Coomassie blue staining (Top and left panel). Molecular weight marker and recombinant GST protein size are indicated on the left of panel. FIG. 3C shows the position of each epitope for anti-AITR antibodies (A27, A35, A41, B32, and B62) within the amino acid sequence of AITR-extracellular domain (ECD) (SEQ ID No.1). Together, FIG. 3A-C show the epitope mapping of the anti-AITR mAbs of the present invention.

FIGS. 6A, 6B and 6C show the induction of expression of $T_H$ lineage-specific marker in CD4+ T cells. Purified CD4+ T cells were stimulated with anti-CD3/IL-2 for 3 days (FIG. 6A), and treated with anti-AITR mAbs (FIG. 6B) or AITR ligand (FIG. 6C) for additional 7 days. The cultured cells were stained for endogenous IL-4, IFN-γ, and IL-17A, and the surfaces thereof were stained with PE-conjugated anti-AITR mAb (clone A41). Then the cells were analyzed by flow cytometry. The experimental result shown is based on one of the three independent experiments.

FIG. 7A shows the western blotting analysis demonstrating the expression of TRAFs. After 24 hr of culturing, the cultured cells were lysed and immunoprecipitated with anti-AITR mAbs (clones A27, A35 and A41) and Protein G. Then the immunoprecipitates were immunoblotted with anti-TRAF1, anti-TRAF2, anti-TRAF3, anti-TRAF5, anti-TRAF6, or anti-AITR mAb (clones A27, A35 and A41). FIG. 7B shows the western blotting analysis demonstrating the expression of NFAT1/2, p-p38, p-ERK1/2, p-JNK1/2, and p-NF-KB. The cells were treated with anti-AITR mAbs for the indicated times and lysed. Then the cell lysates were analyzed by western blotting using the antibodies against NFAT1/2, p-p38, p-ERK1/2, p-JNK1/2, and p-NF-KB. The expression level of the target proteins was normalized to β-actin expression level. FIG. 7C shows the flow cytometry analysis showing the expression of STATs. After 24 hours of culturing, the cells were analyzed by flow cytometry using the antibodies against p-STAT-1, p-STAT-3, p-STAT-4, p-STAT-5 and p-STAT-6.

FIG. 8 shows the recruitment of TRAF protein and activation of signal transduction molecule by anti-AITR mAb in CD4+ T cell and $T_{reg}$ cell.

FIG. 9 shows the activation of STAT protein and master transcription factor by anti-AITR mAb in CD4+ T cell and $T_{reg}$ cell.

FIG. 12A shows the analysis of the effector phenotypes of cytokines. CD4+CD25$^{high}$ T cells isolated from healthy subjects were treated with anti-AITR mAbs for 7 days. The cultured cells were stained for endogenous cytokines IFN-γ, IL-4, and IL-17A, and the effector phenotypes were examined by flow cytometry. FIG. 12B shows the measurements of the expression level of cytokines. The cell cultures were collected at the indicated times and the level of TGF-β, IFN-γ, IL-4, and IL-17A cytokines therein was measured. FIG. 12C shows the measurements of the expression level and mean fluorescence intensity (MFI) of master transcription factors. The isolated CD4+CD25high T cells were stimulated with anti-AITR mAbs. The CD4+CD25$^{high}$ cells stimulated with anti-AITR mAbs were collected at the indicated times and stained with the antibodies against T-bet, RORγt, GATA-3 and Foxp3. The expression level and mean fluorescence intensity (MFI) of these transcription factors were measured by using flow cytometry. FIG. 12D shows the analysis of the effector phenotypes of master transcription factors. The CD4+CD25high T cells isolated from cancer patients were stimulated with anti-AITR mAbs for 7 days. Subsequently, the treated cells were stained for endogenous cytokines IFN-γ, IL-4, and IL-17A, and the effector phenotypes thereof were analyzed by flow cytometry. The cells were sorted by using flow cytometry, which were then treated with anti-AITR mAbs for 7 days. The level of endogenous cytokines IFN-γ, IL-4, and IL-17A in the cultured cell was measured by using flow cytometry. The number of cell populations was calculated. The data represents the results from three independent experiments (mean±SD). *p<0.05 (compared to other groups). Together, FIG. 12A-D show the AITR-mediated conversion of human $T_{reg}$ cell to $T_H1$ or $T_H17$ cell. The sample of CD4+ T cells isolated from healthy subjects and cancer patients were treated with anti-CD3/IL-2 for 2 days for activation.

FIG. 13A and FIG. 13B show the AITR-mediated conversion of human $T_{reg}$ cells isolated from healthy subjects to T$_H$17 cells. CD4$^+$ T cells purified from healthy subjects were stimulated with anti-CD3/IL-2 for 5 days.

FIG. 14A and FIG. 14B show the recruitment of TRAFs and activation of other signal molecules in CD4$^+$CD25$^{high}$ T cells by anti-AITR mAbs. The sorted CD4$^+$CD25$^{high}$ T cells were stimulated with anti-AITR mAbs for 6, 12, or 24 hours.

FIG. 15B shows the flow cytometry analysis of T-bet, GATA-3, RORγt and Foxp3. Culture cells were collected at the indicated times and stained with T-bet, GATA-3, RORγt and Foxp3 antibodies, and then analyzed by flow cytometry. One of the three independent experimental results is shown. Together, FIG. 15A and FIG. 15B show the induction and activation of STAT proteins and master transcription factors in CD4$^+$CD25$^{high}$ T cells by anti-AITR mAbs. The sorted CD4$^+$CD25$^{high}$ T cells were stimulated with anti-AITR mAbs.

BEST MODE

Figure 2A:
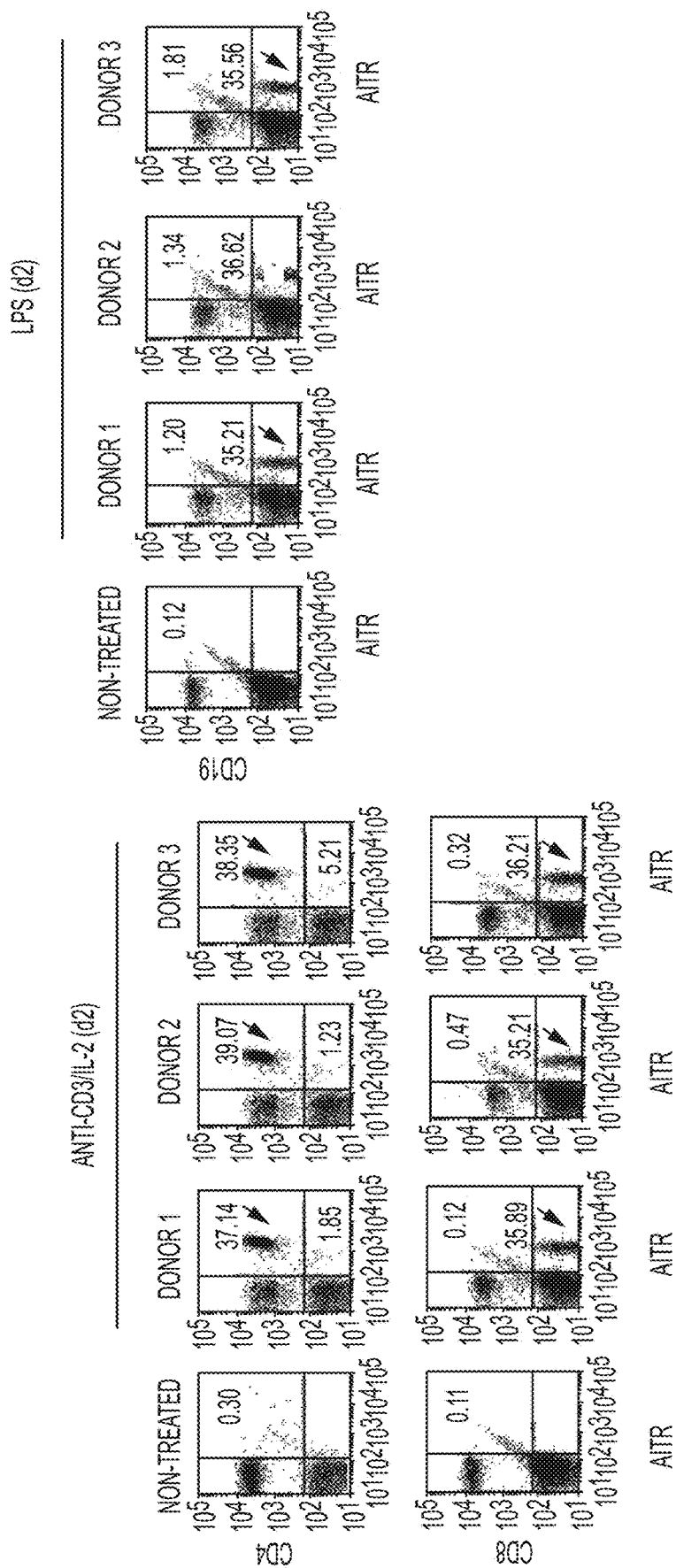
FIG. 2A shows the stimulated cells stained with PE-conjugated anti-AITR mAb (clone A41) in a test group of CD4$^+$, CD8$^+$, and CD19$^+$ cells. Expressions of AITR (arrow pointing) in CD4$^+$ T cells (upper panels), CD8$^+$ T cells (middle panels), and CD19$^+$ cells (down panels) were detected by staining both of the non-treated group or activated group of cells.
Figure 2B:
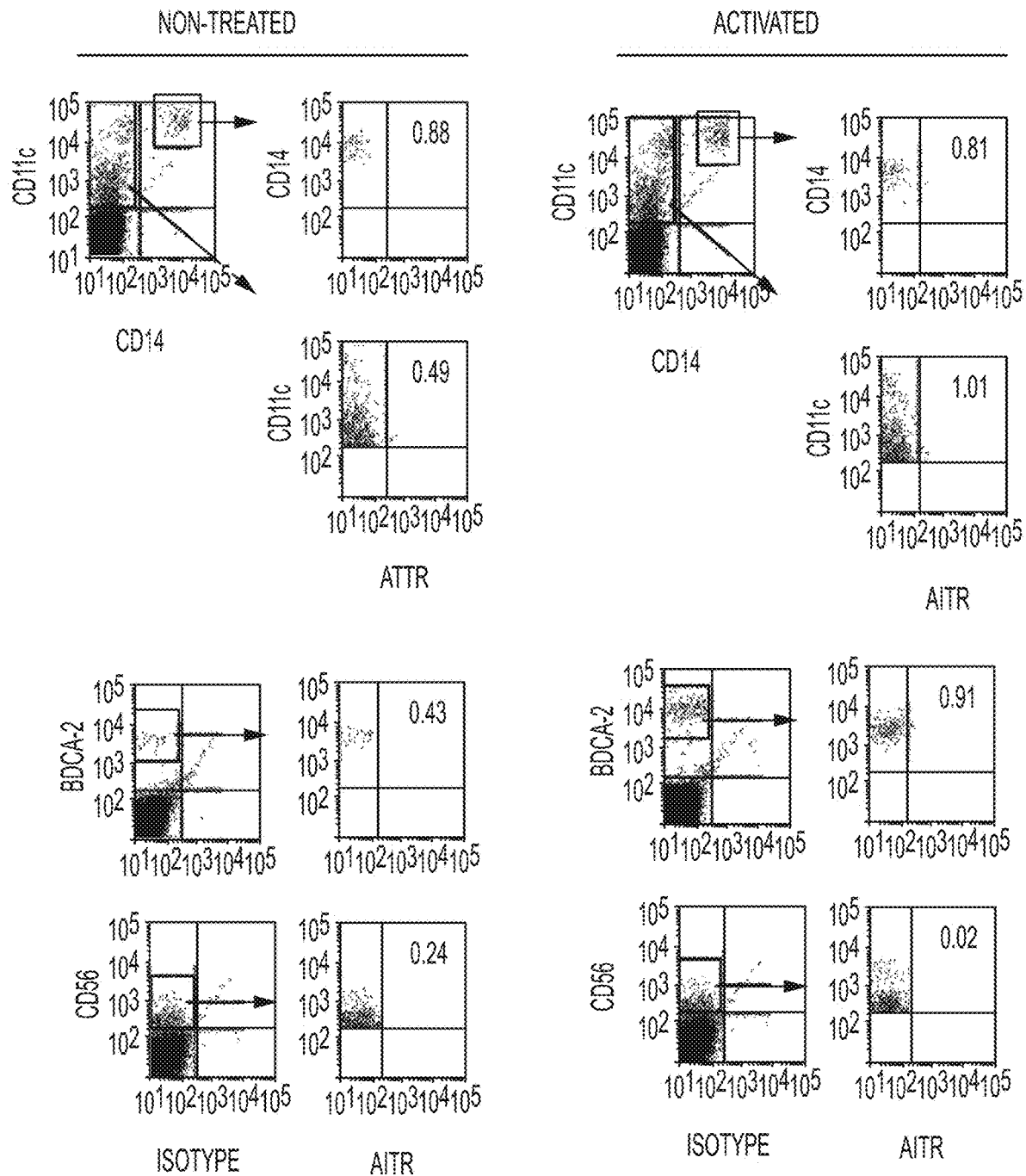
FIG. 2B shows the stimulated cells stained with PE-conjugated anti-AITR mAb in a group of CD11c$^+$CD14$^+$, BDCA-2$^+$ and CD56$^+$ cells. Expressions of AITR were detected by staining the non-treated group (left panels) or activated group (right panels). The representative flow cytometric profiles are shown as dot plot diagrams. The proportion of AITR-expressing cells in each cell population is indicated. One of the results from three independent experiments is shown in this figure. Together.

As one aspect, the present invention provides a polypeptide defined by an amino acid sequence of SEQ ID No.2, which is an epitope of activation-inducible tumor necrosis factor receptor (AITR), for converting T cell to type 17 helper T (T$_H$17) cell.

As used herein, "activation-inducible tumor necrosis factor receptor (AITR)" refers to a type of receptor belonging to TNFR superfamily, and can be interchangeably used with glucocorticoid-induced TNFR-related protein (GITR), tumor necrosis factor receptor superfamily member 18 (TNFRSF18), or CD357. The AITR may preferably be human AITR, but is not limited thereto. Information on AITR can be obtained from a well-known database such as NCBI GenBank. For instance, the information on AITR may be found by searching with NCBI Reference Sequence: NP_004186, but is not limited thereto. The AITR is expressed constitutively at high level in activated T cell or T$_{reg}$ cell.

As used herein, the term "epitope" refers to a site on antigen determining the antigen specificity, and can be interchangeable used with antigen determining group or antigen determining site. For the purpose of the present invention, the epitope refers to the site corresponding to 41$^{st}$ to 50$^{th}$ amino acids of AITR-ECD, which can convert T cell to T$_H$17 cell, but is not limited thereto as long as the sequence has the same converting activity. Also, the scope of the epitope may include the sequence having at least 80%, 90%, 95%, 98%, or 99% sequence homology to the sequence of 41st to 50th amino acids of AITR-ECD without limitation, as long as it has the same activity as the above-specified sequence. The sequence of 41$^{st}$ to 50th amino acids of AITR-ECD is shown in FIG. 3 and Table 2, and named as SEQ ID No.2. The present inventors identified for the first time that the sequence of 41st to 50th amino acids of AITR represented by an amino acid sequence of SEQ ID No.2 is the part that can induce the conversion of T cell T$_H$17 cell. In an effort to identify a specific site that can specifically convert T cell to T$_H$17 cell in AITR-ECD constituted of 139 amino acids (SEQ ID No.1), the present inventors have confirmed that when the cell is treated with an antibody recognizing the sequence of 41st to 50th amino acids represented by SEQ ID No.2 as an epitope, it can specifically convert T cell to T$_H$17 cell. On the other hand, for other sites adjacent to 41st to 50th amino acids, they did not show the converting activity to T$_H$17 cell unlike the site of 41st to 50th amino acids, and thus it was identified that the sequence of 41st to 50th amino acids of AITR-ECD is highly specific for cell conversion to T$_H$17 cell (Experimental Examples 2 and 4 to 8).

As used herein, "conversion of T cell to type 17 helper T (T$_H$17) cell" refers to converting T cell to T$_H$17 cell through antibody binding to a specific epitope of AITR represented by SEQ ID No.2 or non-antibody protein specifically binding to the same. Preferably the conversion refers to the conversion of T cell to T$_H$17 producing IL-17A through an antibody binding to the epitope of AITR in T cell represented by SEQ ID No.2, but is not limited thereto. The conversion of T cell to T$_H$17 can be identified by observing the expression or secretion of T$_H$17 cell-specific marker, for example cytokines such as IL-17A; activation of NFAT1/STAT-3 signal transduction pathway; and expression of transcription factor such as RORγt.

The T cell refers to a T cell expressing AITR protein, and for example it may be the activated T cell or regulatory T cell. In one example of the present invention, it was identified that CD4$^+$ T cell and regulatory T cell expressed AITR when stimulated by anti-CD3/IL-2 or LPS. Also, the T$_H$17 cell is an immune cell secreting IL-17A and mediates immune response against bacteria and fungus. Therefore, a polypeptide of the present invention which is an epitope of AITR represented by SEQ ID No.2 that can convert T cell to T$_H$17 cell can be effectively used in the development of antibody for preventing or treating infectious disease.

In the conversion of the T cell to T$_H$17 cell, T cell may be a regulatory T (T$_{reg}$) cell.

As used herein, "T$_{reg}$ cell" refers to a subpopulation of T cell that can down regulate immune system. Also, a regulatory T cell can be interchangeably used with T$_{reg}$ cell, CD4$^+$CD25$^{high}$ cell, or CD4$^+$CD25$^{high}$Foxp3$^+$ cell. The T$_{reg}$ cell comprises both of natural or constitutive regulatory T cell and adaptive or inducible regulatory T cell.

The signaling pathway and transcription factors associated with T$_H$17 differentiation are involved in the conversion of the T$_{reg}$ cell to T$_H$17 cell. In particular, Foxp3 transcription factor is an intrinsic marker specific to T$_{reg}$ cell, and when T$_{reg}$ cell differentiates to T$_H$17 cell, the cellular level of Foxp3 gets reduced. On the other hand, the level of RORγt which is involved in T$_H$17 cell differentiation is increased through NFAT1/STAT-3 pathway.

Figure 10:
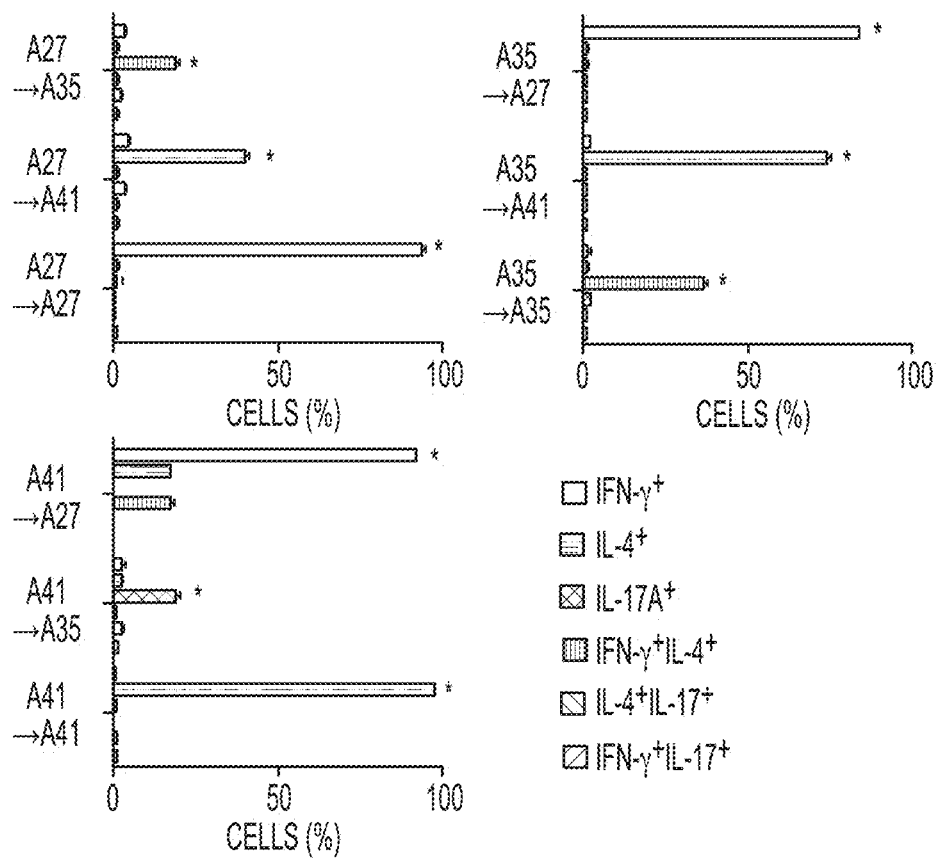
FIG. 10 shows the switching effect of anti-AITR mAbs in CD4+ T cells. Purified CD4+ T cells were stimulated with anti-CD3/IL-2 for 3 days for activation. Then the cells were further treated with anti-AITR mAbs for additional 7 days. Subsequently, the treated cells were washed and re-stimulated with media comprising the antibodies having different or same epitopes for 7 days. The cells were stained for endogenous cytokines IFN-γ, IL-4, and IL-17A. Then the effector phenotypes were examined. Also, the number of cell populations was calculated. Data shown are the average of three independent experimental results (mean±SD), single asterisk, *p<0.05 (compared to other groups).
Figure 11:
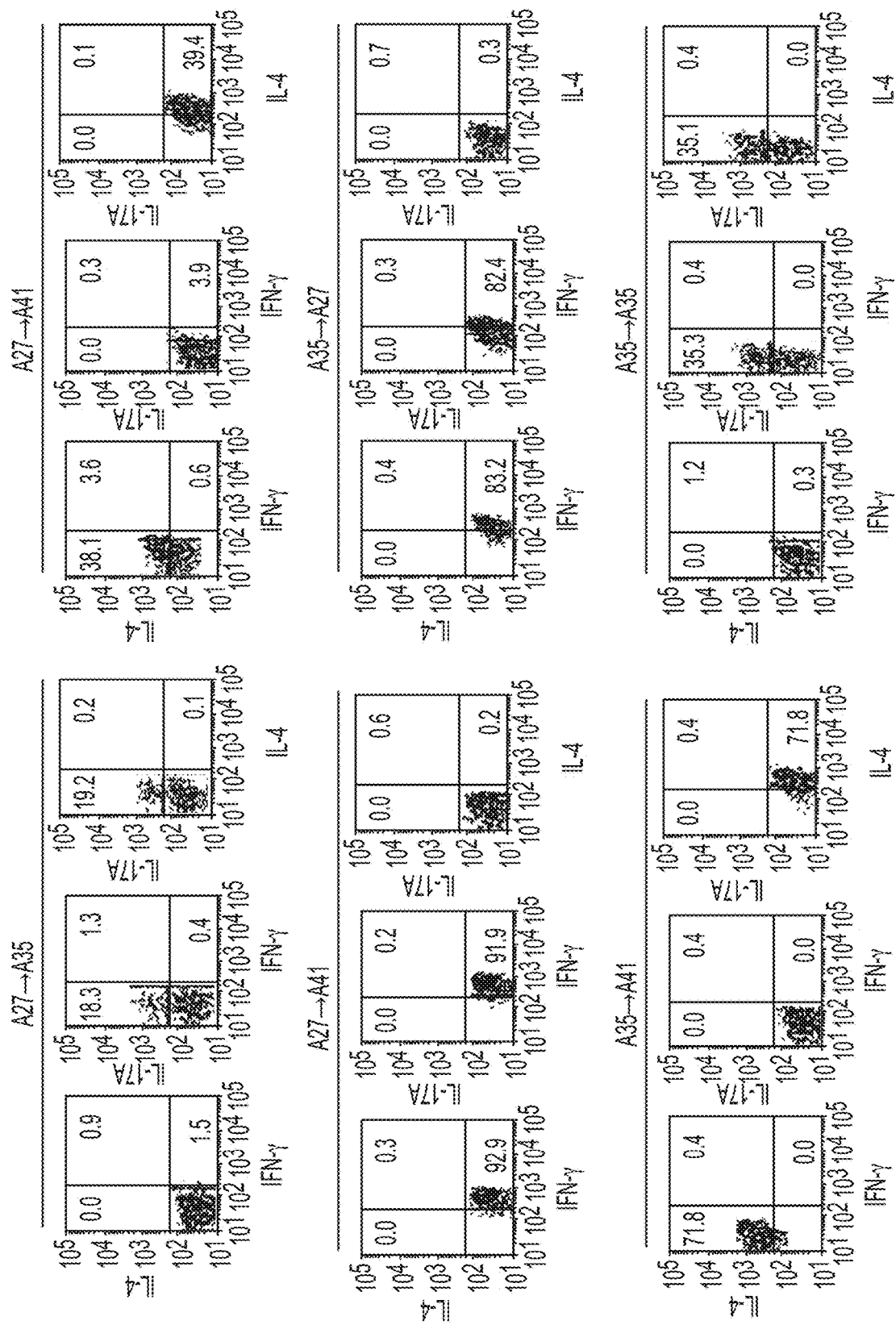
FIG. 11 shows the switching effect of anti-AITR mAbs in CD4+ T cell.
Figure 11:
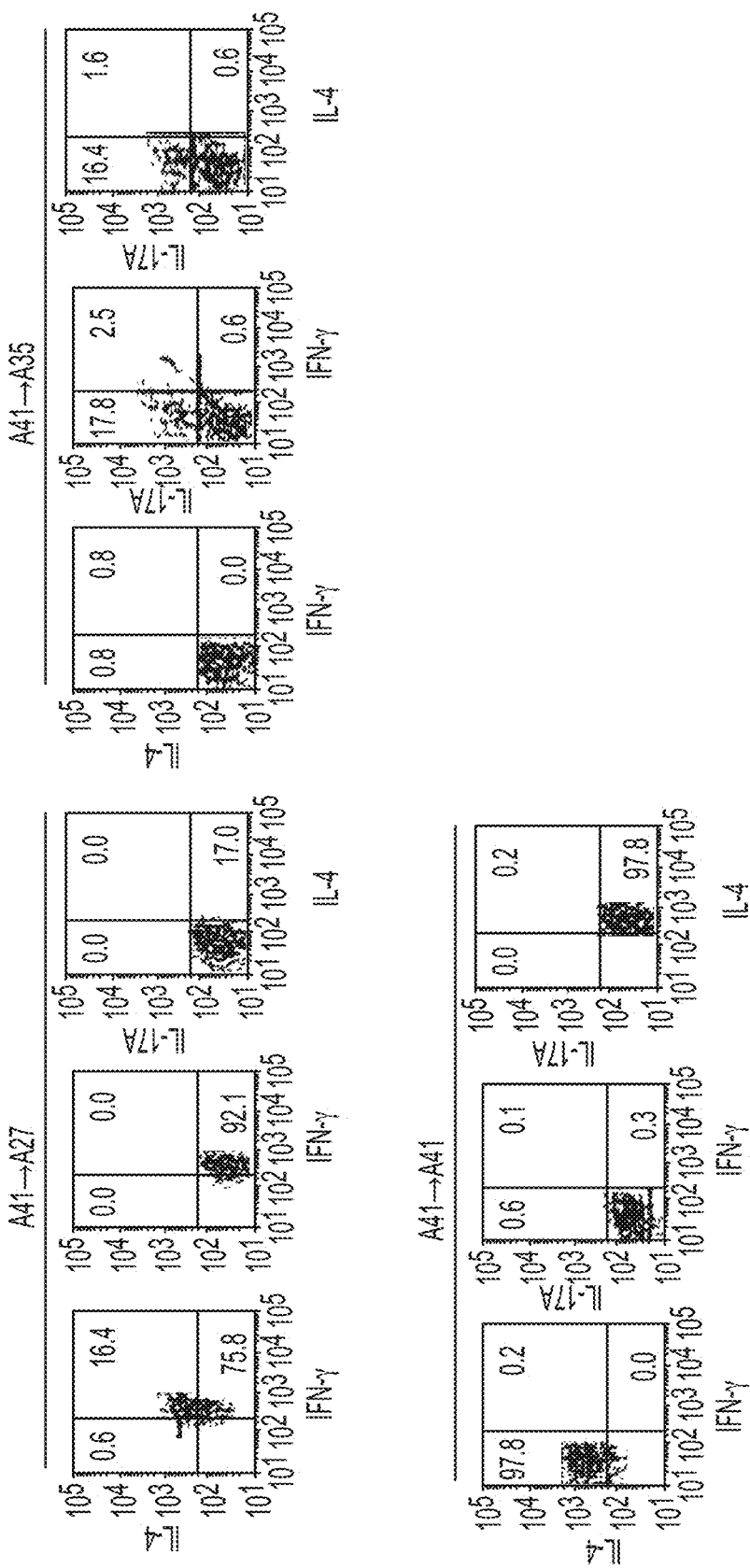
Figure 13A:
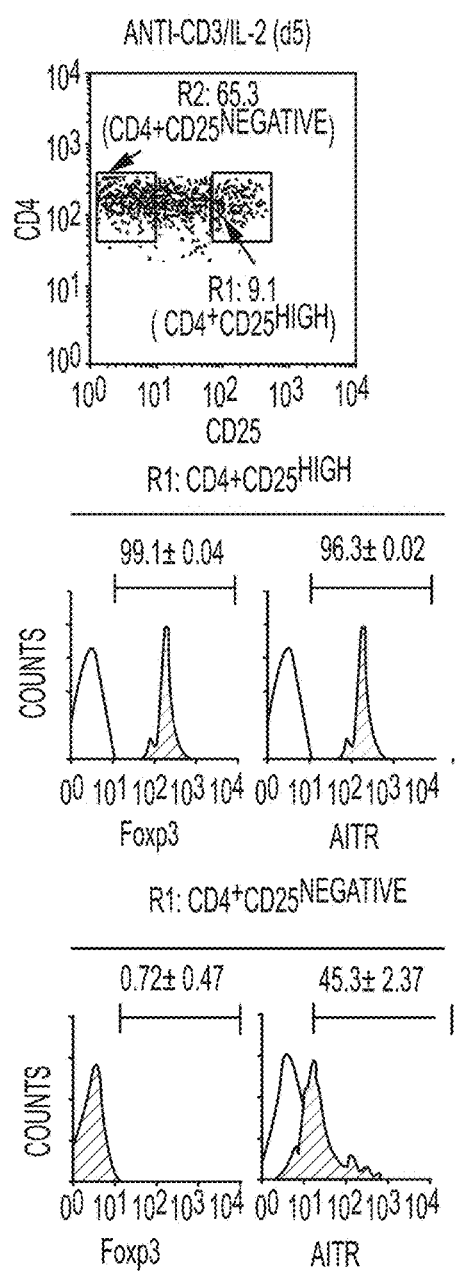
FIG. 13A shows the expression of AITR and Foxp3 in CD4+CD25$^{high}$T cells (R1) and CD4+CD25− T cells (R2). CD4+CD25$^{high}$ T cells (R1) and CD4+CD25− T cells (R2) were sorted by FACS sorter which is a flow cytometry. Then the expression of AITR and Foxp3 was detected in the sorted cells.
Figure 13B:
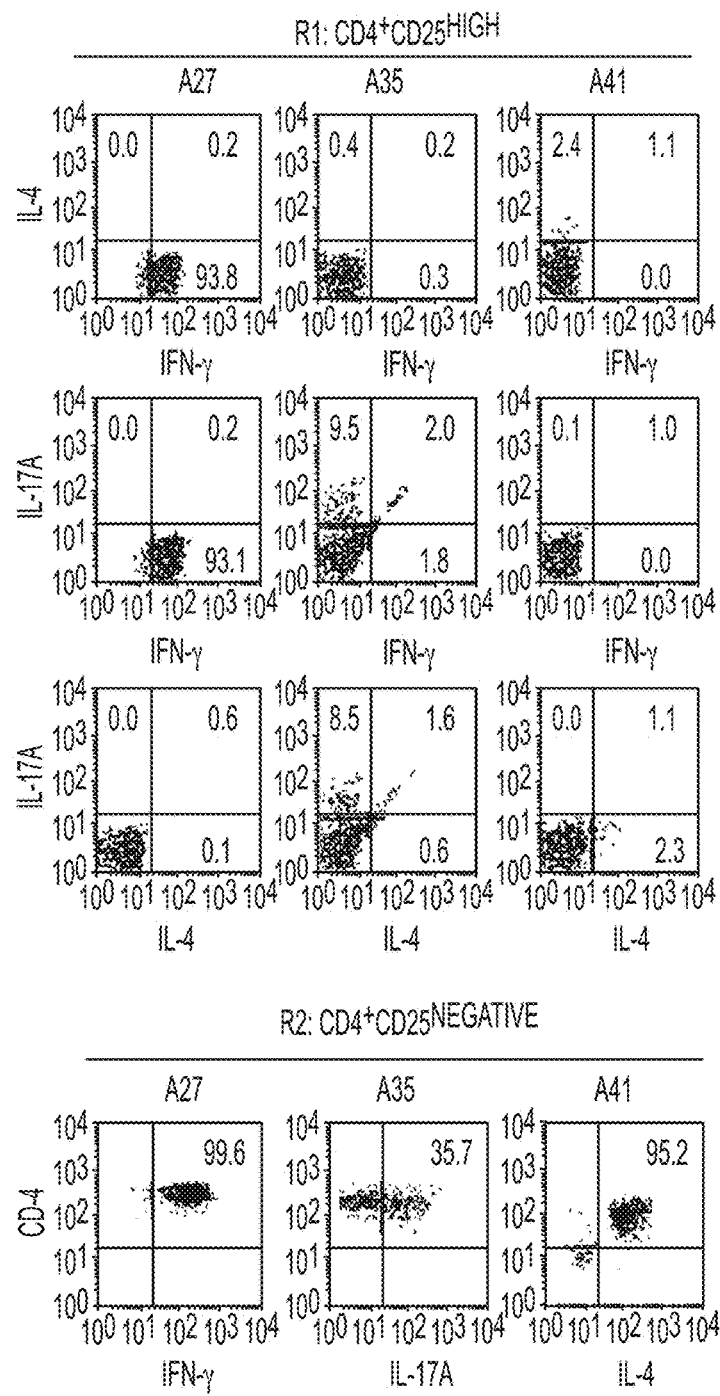
FIG. 13B shows the analysis of effector phenotype of CD4+CD25$^{high}$ T cells and CD4+CD25− T cells. The sorted CD4+CD25$^{high}$ T cells and CD4+CD25− T cells were stimulated with anti-AITR mAbs. The stimulated cells were stained for endogenous cytokines IL-4, IFN-γ, and IL-17A and were examined for effector phenotype by flow cytometry. One of the three independent experimental results is shown. Together.
Figures 14A, 14B:
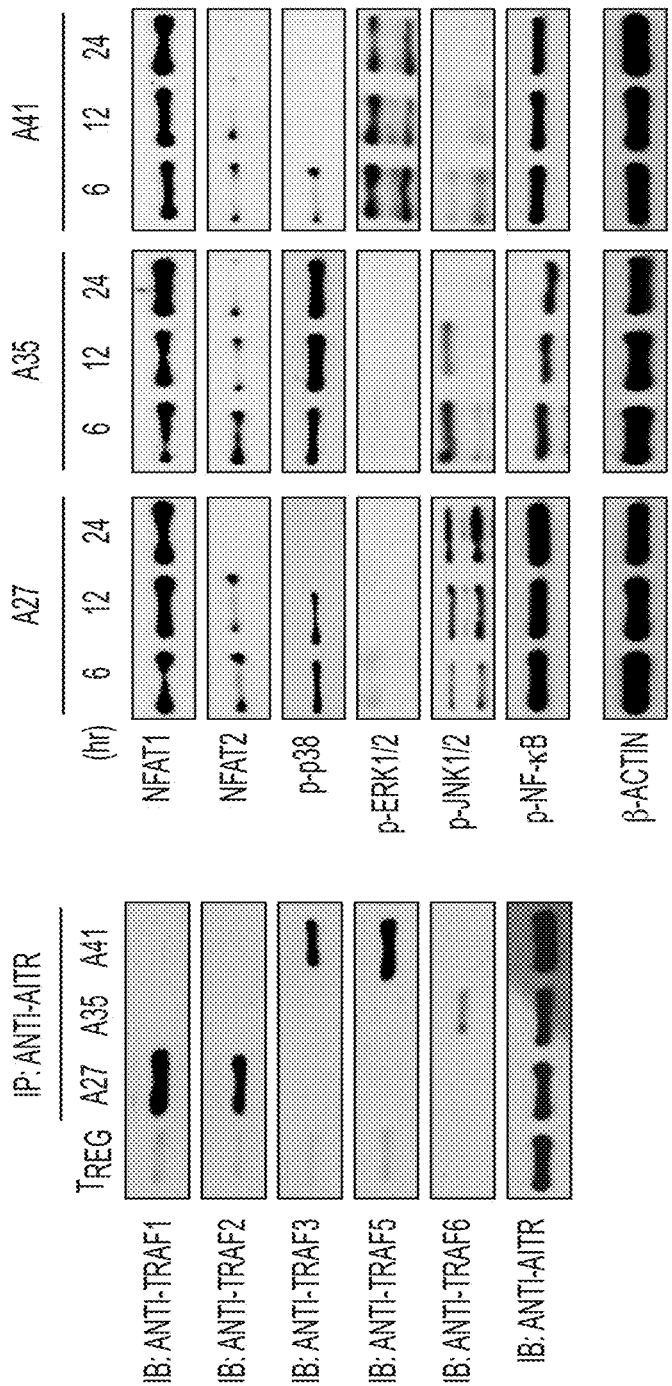
FIG. 14A shows the western blotting analysis of CD4$^+$CD25$^{high}$ T cells for the expression of TRAF proteins. After 24 hours of culturing, cell lysates were prepared, which were then immunoprecipitated with protein G. The immunoprecipitates were immunoblotted with anti-TRAF1, 2, 3, 5 and 6, or anti-AITR mAb.
FIG. 14B shows the western blotting analysis of CD4$^+$CD25$^{high}$ T cell lysates prepared at the indicated times for the expression of NFAT1/2, p-p38, p-ERK1/2, p-JNK1/2, p-NF-KB, or β-actin. The results were normalized according to the level of β-actin expression. Data shown here are representative of three independent experiments. Together.
Figure 15A:
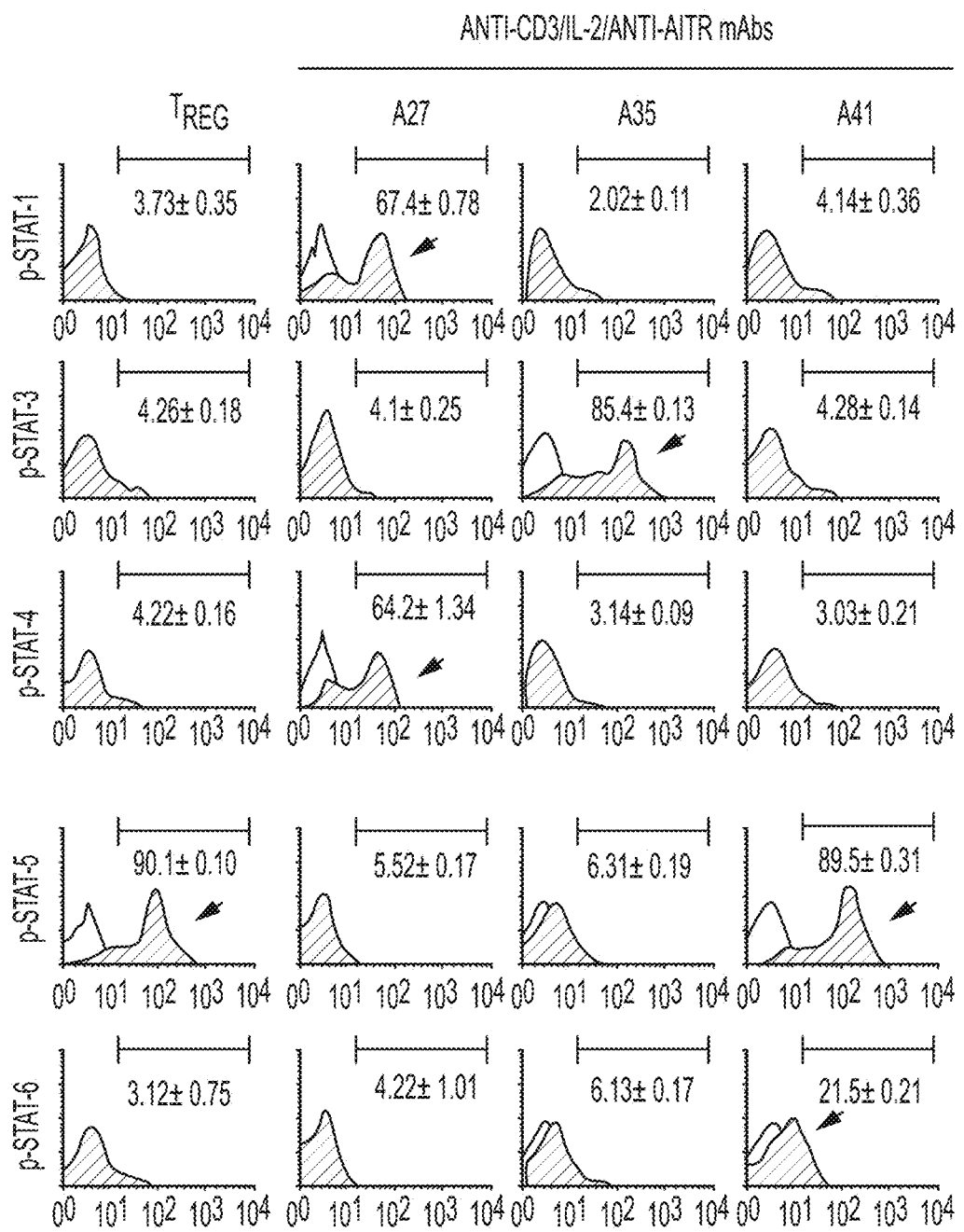
FIG. 15A shows the analysis of STAT protein expression. After 24 hours of culturing, the cultured cells were analyzed by flow cytometry using the antibodies against p-STAT-1, p-STAT-3, p-STAT-4, p-STAT-5 and p-STAT-6. Expressions of STAT proteins are shown as filled histograms (arrow pointing) in comparison to the control group (unfilled histogram). Data are representative of three independent experiments (mean±SD)

In one example of the present invention, it was confirmed that T$_{reg}$ cell was differentiated into T$_H$17 cell by A35 which is a representative antibody of the present invention that specifically recognizes the epitope of SEQ ID No.2. However, other AITR-specific antibody recognizing the site other than the epitope of SEQ ID No.2 did not show the above converting activity. To be specific, A27 antibody recognizing the sequence of $56^{st}$ to $65^{th}$ amino acids and A41 antibody recognizing the sequence of 20th to 30th amino acids could not differentiate T cell to $T_H17$ cell, even though these epitope sites were significantly close to the sequence of $41^{st}$ to 50th amino acids of AITR-ECD (FIGS. 3, 4, and 6 to 15). In addition, even after the T cell was converted to the cells that secrete a specific cytokine through treatment with A27 or A41, the cell could be re-converted to IL-17A-secreting cell, when treated with A35 antibody recognizing the epitope of SEQ ID No.2 of the present invention. These results suggest that the epitope of SEQ ID No.2 is significantly important site in cell conversion to $T_H17$ cell (FIGS. 10 and 11). Also, in one example of the present invention, a molecular mechanism behind the conversion to $T_H17$ cell through an epitope of SEQ ID No.2 was investigated, and it was confirmed that the antibody of the present invention that specifically recognizes the epitope of SEQ ID No.2 can convert the T cell to $T_H17$ cell. To be specific, in the present invention it was identified that a main transcription factor, NFAT1, is involved in the conversion to $T_H17$ cell and that the antibody of the present invention increased the phosphorylation level of STAT-3 protein which takes an important role in signal transduction of $T_H17$ cell (FIGS. 7 to 9, 14, and 15). In addition, it was observed that a representative antibody of the present invention, A35, increased the level of RORγt which is a $T_H17$ cell-specific marker, thereby confirming that $T_{reg}$ cell could be efficiently converted to $T_H17$ cell (FIGS. 12 and 15).

As another aspect, the present invention provides an antibody specifically recognizing an epitope of activation-inducible tumor necrosis factor receptor (AITR), wherein the epitope is represented by SEQ ID No.2.

As used herein, the term "antibody" refers to a protein molecule that acts as a receptor recognizing an antigen specifically, comprising an immunoglobulin molecule that responses to a specific antigen immunologically. Also, the antibody comprises all of polyclonal antibody, monoclonal antibody, whole antibody, and antibody fragment. In addition, the scope of antibody includes a chimeric antibody (for example, humanized murine antibody) and bivalent or bispecific molecule (for example, bispecific antibody), diabody, triabody, and tetrabody. The whole antibody is constituted of two full-length light chains and two full-length heavy chains, wherein each of the light chains is connected with heavy chains through disulfide binding. The whole antibody comprises IgA, IgD, IgE, IgM, and IgG. IgG comprises IgG1, IgG2, IgG3, and IgG4 as subtypes thereof. The antibody fragment refers to a fragment capable of binding to antigen, and it comprises Fab, Fab', F(ab')2, and Fv. The Fab is constituted of variable regions of light chain and heavy chain, constant region of light chain, and the first constant region of heavy chain (CH1 domain), having one antigen-binding site. Fab' is different from Fab in that it has a hinge region which comprises more than one cysteine residue at C-terminal of heavy chain CH1 domain. F(ab')2 antibody is formed through disulfide bonding of cysteine residues in the hinge region of Fab'. A variable fragment (Fv) refers to a minimized antibody fragment having heavy chain variable region and light chain variable region. In a double stranded Fv (dsFv), heavy chain variable region and light chain variable region are connected through disulfide bonding while in a single stranded Fv (scFv), heavy chain variable region and light chain variable region are covalently bonded through peptide linker. These antibody fragments can be obtained by treating the antibody with protease (for example, when a whole antibody is restriction digested with papain, Fab is obtained and when restriction digested with pepsin, F(ab')2 fragment can be obtained). Preferably, the antibody fragment can be generated by using genetic recombination technique.

As used herein, the term "monoclonal antibody" refers to an antibody molecule that has been obtained from a substantially identical antibody clone, which shows single-binding specificity and affinity for a specific epitope.

Typically, immunoglobulin has heavy chain and light chain and each of the heavy chain and light chain possesses constant region and variable region (also known as domains). A variable region of light chain and heavy chain comprises three variable regions and four framework regions called complementarity-determining region (hereinafter referred to as "CDR"). The CDR mainly acts to bind to an epitope of antigen. CDRs of each chain is conventionally called CDR1, CDR2, and CDR3 successively starting from the N-terminal, and also they are distinguished by the chain at which they are located.

As used herein, the term "human antibody" refers to a molecule derived from human immunoglobulin, in which all of the amino acid sequences constituting the antibody including complementarity-determining regions and framework regions are composed of amino acid sequences of human immunoglobulin. Human antibody is conventionally used for treating human diseases, which has more than three potential advantages. First, human antibody interacts more favorably with human immune system, and thus it can destroy the target cell more efficiently, for example through complement-dependent cytotoxicity (CDC) or antibody-dependent cell-mediated cytotoxicity (ADCC). Secondly, human immune system does not recognize the human antibody as a foreign substance. Thirdly, when smaller dose of drug was administered at lower frequency, half-life of human antibody in human circulation is similar to that of naturally-occurring antibodies. In one example of the present invention, it was confirmed that a human monoclonal antibody specifically recognizing the epitope of SEQ ID No.2 demonstrates a strong affinity toward AITR and thus can effectively convert T cell to $T_H17$ cell (FIGS. 1, 3, 4, and 6 to 15). The heavy chain and light chain domains of the antibody capable of converting T cell to $T_H17$ cell effectively are all human-derived showing lower rate of immunogenicity, and thus the antibody can be effectively used for treating infectious disease.

As used herein, "antibody specifically recognizing an epitope of activation-inducible tumor necrosis factor receptor (AITR) represented by SEQ ID No.2" refers to an antibody that can convert T cell to $T_H17$ cell by specifically recognizing an epitope of SEQ ID No.2, but is not limited thereto. The antibody can particularly convert $T_{reg}$ cell to $T_H17$ cell, and thus it can be effectively used for preventing or treating infectious disease; and for enhancing immunity.

The antibody specifically recognizing the epitope of SEQ ID No.2 may preferably comprise a heavy chain variable region comprising heavy chain complementarity-determining region 1 (CDR1) represented by SEQ ID No.6; heavy chain CDR2 represented by SEQ ID No.7; and heavy chain CDR3 represented by SEQ ID No.8, and a light chain variable region comprising light chain CDR1 represented by SEQ ID No.10; light chain CDR2 represented by SEQ ID No.11; and light chain CDR3 represented by SEQ ID No.12. More preferably, the antibody may comprise an amino acid sequence of heavy chain variable region represented by SEQ ID No.5 and an amino acid sequence of light chain variable region represented by SEQ ID No.9; or an amino acid sequence of heavy chain variable region represented by SEQ ID No.15 and an amino acid sequence of light chain variable region represented by SEQ ID No.16, but is not limited thereto. In one example of the present invention, a human monoclonal antibody comprising the amino acid sequence of heavy chain variable region represented by SEQ ID No.5 and the amino acid sequence of light chain variable region represented by SEQ ID No.9 was named as A35. In addition, a human monoclonal antibody comprising an amino acid sequence of a heavy chain variable region represented by SEQ ID No.15; and an amino acid sequence of a light chain variable region represented by SEQ ID No.16 was named as B62.

Nucleic acids encoding the antibody may comprise the nucleic acids encoding a heavy chain variable region represented by SEQ ID No.13 and nucleic acids encoding a light chain variable region represented by SEQ ID No.14; or the nucleic acids encoding a heavy chain variable region represented by SEQ ID No.17 and nucleic acids encoding a light chain variable region represented by SEQ ID No.18, but are not limited thereto.

Likewise, in the present invention it was confirmed that even when the antibodies consist of different sequences to each other, if those antibodies specifically recognize the epitope of SEQ ID No.2, they can convert T cell specifically to $T_H17$ cell, and that the antibodies can be effectively used for the prevention or treatment of infectious disease, and for the enhancement of immunity.

In addition, if the antibody of the present invention comprises a constant region, the constant region may be derived from IgG, IgA, IgD, IgE, and IgM or a combination or hybrid thereof.

As used herein, the term "combination" refers to, when forming a dimer or polymer, a combination of a polypeptide coding for single-chain immunoglobulin constant region of same origin with single-chain polypeptide of different origin. For example, the dimer or polymer can be formed with more than two constant regions selected from the group consisting of constant regions of IgG, IgA, IgD, IgE, and IgM.

As used herein, the term "hybrid" refers to the presence of more than two immunoglobulin heavy chain constant regions of different origins within a single-chain immunoglobulin heavy chain constant region. For example, a hybrid of domains can be formed with 1 or 4 domains selected from the group consisting of CH1, CH2, CH3, and CH4 of IgG, IgA, IgD, IgE, and IgM. Meanwhile, a combination or hybrid of heavy chain constant regions of the subtypes of IgG such as IgG1, IgG2, IgG3, and IgG4 is also possible. The combination and hybrid are the same as described above.

Also, if the antibody of the present invention comprises a light chain constant region, the light chain constant region may be derived from lambda (λ) or kappa (κ) light chain.

In one example of the present invention, A35 and B62 that specifically bind to AITR were selected from a human antibody library (Experimental Example 1), and their specific binding to AITR was confirmed (FIG. 1). In addition, the antibody recognition sites on AITR-ECD were identified (FIG. 3 and Table 2). Also, it was confirmed that unlike other antibodies that recognize other sites of AITR, the above-described antibodies can convert T cell to $T_H17$ cell (FIGS. 3, 4, and 6 to 15), and furthermore, even the T cells that were already differentiated into specific T cell lineage, the antibodies can re-convert those cells to $T_H17$ cell (Experimental Examples 7 and 8, and FIGS. 10 and 11). These results support that the AITR-specific antibody of the present invention that recognizes an epitope of SEQ ID No.2 can efficiently convert T cell, particularly $T_{reg}$ cell, to $T_H17$ cell, and having this activity, it can be effectively used for prevention or treatment of infectious disease and enhancement of immunity.

As another aspect, the present invention provides a method for preparing the antibody.

The antibody of the present invention can be easily prepared by a conventional method for production of antibody. For example, a monoclonal antibody can be prepared by generating hybridoma with B lymphocyte obtained from immunized animals (Koeher and Milstein, 1976, Nature, 256:495), and phage display technique, but is not limited thereto. A polyclonal antibody can be easily prepared by a conventional method for production of antibody, and also it can be prepared by using an antigen comprising the epitope of the present invention.

Production of antibody library by using phage display technique is done by obtaining an antibody gene directly from B lymphocyte without producing hybridoma and expressing the antibody on the phage surface. By using the phage display technique, many limitations associated with the production of monoclonal antibody can be overcome by B-cell immortalization. In general, a phage display technique consists of the steps of (1) inserting oligonucleotides of random sequences to the nucleotide sequence corresponding to N-terminal of phage coat protein pIII (or pIV); (2) expressing a fusion protein of a partial naive coat protein and a polypeptide coded by the oligonucleotide of random sequence; (3) treating a receptor material that can bind to the polypeptide coded by the oligonucleotide; (4) eluting the peptide-phage particles bound to receptors by lowering pH or using competitive molecules for binding to the receptors; (5) amplifying a phage sample eluted by panning within the host cells; (6) repeating the above process to obtain desired amount of phage products; and 7) determining the sequence of active peptide among the DNA sequences of phage clones selected by panning.

Preferably, production of a monoclonal antibody of the present invention can be done by using phage display technique. Those skilled in the art can easily perform each step of the preparation method of the present invention according to a conventional phage display technique, for example a method described in Barbas et al. (METHODS: A Companion to Methods in Enzymology 2:119, 1991; J. Virol. 2001 July; 75(14):6692-9) and Winter et al. (Ann. Rev. Immunol. 12:433, 1994). A type of phage that can be used for generating antibody library includes filamentous phage such as fd, M13, f1, If1, Ike, Zj/Z, Ff, Xf, Pf1, or Pf3 phage, but is not limited thereto. In addition, a type of vector that can be used for expressing heterologous gene on filamentous phage surface includes a phage vector such as fUSES, fAFF1, fd-CAT1, or fdtetDOG or a phagemid vector such as pHENl, pComb3, pComb8, or pSEX, but is not limited thereto. Also, a type of helper phage that can be used for providing a wild-type coat protein which is required for the successful reinfection of recombinant phage for amplification includes M13K07 or VSCM13 helper phage, but is not limited thereto.

The hybridoma-derived monoclonal antibody or polynucleotide encoding phage display clones of the present invention can be easily isolated and analyzed for the sequence thereof through a conventional process. For example, oligonucleotide primers designed to specifically amplify the heavy chain and light chain coding region from hybridoma or phage template DNA can be used. Once the polynucleotide is isolated, it can be inserted to an expression vector, which can be subsequently introduced to a suitable host cell, thereby producing a desired monoclonal antibody from the transformed host cell (i.e., transformant). Therefore, the method for preparing the antibody of the present invention may be a method for preparing antibody comprising the step of amplifying the expression vector comprising polynucleotide encoding the antibody, but is not limited thereto.

As another aspect, the present invention provides a polynucleotide encoding the epitope or antibody, an expression vector comprising the polynucleotide, and a transformant introduced with the vector.

The antibody is the same as described above.

The expression vector of the present invention comprising a polynucleotide encoding the epitope or antibody is not limited to, but may be a vector that can replicate and/or express the polynucleotide in eukaryotic cells including animal cells (for example, human, monkey, rabbit, rat, hamster, and mouse cell etc), plant cell, yeast cell, insect cell, or bacterial cell (for example, E. coli), or prokaryotic cells. Preferably, the vector may be a vector wherein the nucleotide is operably linked to a suitable promoter for the expression thereof in a host cell and at least one selection marker is included. For example, the expression vector of the present invention may be in a form of a phage vector, plasmid vector, cosmid vector, mini-chromosome vector, viral vector, or retroviral vector wherein the polynucleotide is introduced.

The expression vector comprising polynucleotide encoding the antibody may be an expression vector comprising each of polynucleotides encoding the heavy chain or light chain of the antibody, or an expression vector comprising all of polynucleotides encoding heavy chain or light chain.

The transformant of the present invention wherein the expression vector is introduced is not limited to, but may be prepared from bacterial cells such as E. coli, Streptomyces, and Salmonella typhimurium; yeast cells; fungal cells such as Pichia pastoris; insect cells such as Drosophila, Spodoptera Sf9 cell; animal cells such as Chinese hamster ovary (CHO) cells, mouse bone marrow cell SP2/0, human lymphoblastoid, COS, mouse bone marrow cell NSO, 293T, BOW melanoma cell lines, HT-1080, baby hamster kidney (BHK) cells, human embryonic kidney (HEK) cells, human retinal cell PERC.6; or plant cells by transforming the same with the expression vector.

As used herein, the term "introduction" refers to a method of transferring a vector comprising the polynucleotide encoding epitope or antibody to a host cell. Such introduction can be done by using various methods known in the art such as Calcium phosphate-DNA co-precipitation, DEAE-dextran-mediated transfection, polybrene-mediated transfection, electroporation, microinjection, liposome fusion, lipofectamine, and protoplast fusion. Also, transduction refers to a transfer of a target molecule into the cell by using viral particles through infection. Furthermore, a vector can be introduced to the host cell through gene bombardment. In the present invention, the term introduction can be interchangeably used with transfection.

As another aspect, the present invention provides a composition comprising the antibody for converting T cell to type 17 helper T ($T_H17$) cell.

The antibody, T cell, $T_H17$ cell, and conversion of T cell to $T_H17$ cell are the same as described above. The antibody of the present invention specifically recognizing the epitope of AITR represented by SEQ ID No.2 can convert T cell to $T_H17$ cell specifically, and thus a composition comprising the antibody can be used for the conversion of T cell to $T_H17$ cell. Especially, since the composition of the present invention can re-convert the already differentiated cell to $T_H17$ cell, it can be diversely used depending on the purpose.

As another aspect, the present invention provides a method for converting T cell to type 17 helper T ($T_H17$) cell, comprising treating T cell with the antibody.

The antibody, T cell, $T_H17$ cell, and conversion of T cell to $T_H17$ cell are the same as described above. When the T cell, especially regulatory T cell, is treated with the antibody of the present invention, it can be effectively converted to $T_H17$ cell, and thus the antibody can be effectively used in the treatment of diseases that need the function of $T_H17$ cell through converting the cell to $T_H17$ cell.

As another aspect, the present invention provides a pharmaceutical composition for preventing or treating infectious disease, comprising the antibody.

As used herein, the term "infectious disease" refers to a disease caused by pathogenic microorganisms residing and proliferating in the tissue, body fluid, and surface of humans, animals, or plants. Infectious diseases can be divided into different types according to the route of infection and contagiosity thereof. The infection comprises viral infection, fungal infection, bacterial infection, protozoan infection, and parasitic infection, but is not limited thereto.

As used herein, the term "prevention" refers to all actions that suppress or delay the onset of infectious disease by administering a composition.

As used herein, the term "treatment" refers to all actions that can alleviate or beneficially change the symptoms of infectious disease by administering a composition.

The pharmaceutical composition may additionally comprise a pharmaceutically acceptable carrier.

As used herein, the term "pharmaceutically acceptable carrier" refers to a carrier or diluent that does not inhibit a biological activity and feature of the administered compound without irritating an organism. Types of pharmaceutical carriers suitable for a composition of liquid formulation include saline solution, sterile water, Ringer's solution, buffered saline solution, albumin solution, dextrose solution, maltodextrin solution, glycerol, ethanol, and a combination thereof, as a sterilized and acceptable carrier to the organism. If necessary, other conventional additives such as antioxidant, buffer solution, and bacteriostatic agent can be added. Also, the pharmaceutical composition may be formulated into a formulation for injection such as aqueous solution, suspension, emulsion; pill, capsule, granule, and tablet by further adding a diluent, dispersant, surfactant, binder, and lubricant.

The pharmaceutical composition may be in a form of various oral or parenteral formulations. The composition is formulated with conventional diluents or excipients, including fillers, extenders, binders, wetting agents, disintegrants, and surfactants. Solid formulations for oral administration include tablets, pills, powders, granules, and capsules. These solid formulations are prepared by mixing one or more compounds with at least one of excipients, for example, starch, calcium carbonate, sucrose, lactose, and gelatin. Also, other than the simple excipients, lubricants such as magnesium stearate and talc are used. In addition, types of liquid formulation for oral administration include a suspension, solution, emulsion and syrup. To this liquid formulation, not only a commonly used diluent such as water and liquid paraffin may be added, but also various types of excipients such as wetting agents, sweetening agents, flavors, and preservatives can be added. Types of formulations for parenteral administration include sterilized aqueous solutions, non-aqueous solutions, suspensions, emulsions, lyophilized formulation, and suppositories. As non-aqueous solvent and suspending agent, propylene glycol, polyethylene glycol, vegetable oils such as olive oil, and injectable esters such as ethyl oleate may be used. The base composition for suppository may include witepsol, macrogol, tween 61, cacao butter, laurin butter, and glycerinated gelatin.

The pharmaceutical composition of the present invention may be formulated in any one of the forms selected from the group consisting of tablets, pills, powders, granules, capsules, suspension, solutions, emulsions, syrups, sterilized aqueous solution, non-aqueous solution, lyophilized formulation and suppository.

The composition of the present invention is administered in a pharmaceutically effective amount. As used herein, the term "pharmaceutically effective amount" refers to an amount sufficient to treat a disease, at a reasonable benefit/risk ratio applicable to any medical treatment. The effective dosage level of the composition may be determined by the factors including a type of subject, severity of condition, an age and sex of subject, a type of virus, an activity of drug, a sensitivity towards drug, duration and route of administration, excretion rate, duration of treatment, a type of drugs used in combination with the composition, and other factors well-known in the medical field. The composition of the present invention may be administered alone or in combination with other medicines, and it may be administered sequentially or simultaneously with conventional medicines. Also, the present composition may be administered in single or multiple doses. In view of all of these factors, it is important to administer the composition in a minimum amount yielding the maximum possible effect without causing side effects, which can be easily determined by those skilled in the art.

The antibody recognizing the epitope of SEQ ID No.2 of the present invention effectively converts $T_{reg}$ cell having immune suppressive function to $T_H17$ cells that induce immune response. Therefore, as the antibody of the present invention can induce immune response against pathogenic microorganism, it can be effectively used for the treatment of infectious disease.

In one Example of the present invention, it was observed that the antibody of the present invention that binds to the epitope of SEQ ID No.2 efficiently converted T cell to IL-17A-producing $T_H17$ cell (FIGS. 4, and 6 to 15). As described above, the antibody of the present invention can increase the number of $T_H17$ cells that are helpful for the prevention or treatment of infectious disease, and thus it can be effectively used in the prevention or treatment of infectious disease.

As another aspect, the present invention provides a method for treating infectious disease by using the antibody.

The antibody and infectious disease are the same as described above.

The method for treating infectious disease may be a method comprising the step of administering the pharmaceutical composition comprising the antibody and additionally pharmaceutically acceptable carrier to a subject having infectious disease or suspected of having infectious disease. The pharmaceutically acceptable carrier is the same as described above. The method for treating infectious disease may preferably be a method comprising the step of administering the composition comprising the antibody to a subject having infectious disease.

The type of subject includes mammals and birds such as COWS, pigs, sheep, chickens, dogs, and human, and is not limited as long as infectious disease in the subject can be treated by administration of the composition of the present invention.

The composition may be administered in single or multiple doses in a pharmaceutically effective amount. In this regard, the composition may be administered in a form of solutions, powders, aerosols, capsules, enteric-coated tablets or capsules or suppositories. The routes for administration include intraperitoneal, intravenous, intramuscular, subcutaneous, intradermal, oral, topical, intranasal, intrapulmonary and intrarectal administration, but are not limited thereto. However, since peptides are digestible when orally administered, the active ingredients of a composition for oral administration need to be coated or formulated such that they can be protected against degradation in stomach. In addition, a pharmaceutical composition may be administered through a certain apparatus capable of transporting the active ingredients into a target cell.

The pharmaceutical composition of the present invention may comprise an antibody that specifically binds to the epitope of SEQ ID No.2. As described above, as the antibody of the present invention efficiently converts T cell to IL-17A-producing $T_H17$ cell, it can be effectively used in the treatment of infectious disease. Therefore, through administering the pharmaceutical composition comprising the antibody into the body, the onset or progression of infectious disease can be prevented, thereby preventing or treating infectious disease.

As another aspect, the present invention provides a method for enhancing immune response, comprising administering the antibody to a subject in need thereof.

The antibody, subject, and administration are the same as described above. The antibody of the present invention recognizing the epitope of SEQ ID No. 2 converts $T_{reg}$ cell, which suppresses immune response, to $T_H17$ cell that induces immune response by producing IL-17A, and thus by administering the antibodies to a subject, the immune response can be enhanced.

As another aspect, the present invention provides a composition for enhancing immunity, comprising the antibody.

The composition may be in a form of a pharmaceutical composition or a food composition, but is not limited thereto. The pharmaceutical composition is the same as described above.

The food composition comprises the components that are conventionally included in the preparation of food product, for example, protein, carbohydrate, fat, nutrient, seasoning, and flavoring. Examples of such carbohydrate include conventional sugars such as monosaccharide (e.g. glucose and fructose), disaccharide (e.g. maltose, sucrose, oligosaccharide) and polysaccharide (e.g. dextrin, cyclodextrin) and sugar alcohol such as xylitol, sorbitol, and erythritol. As for flavoring, a natural flavoring (e.g. stevia extract such as thaumatin, rebaudioside A, and glycyrrhizin) and a synthetic flavoring (e.g. saccharine and aspartame) may be used.

MODE FOR INVENTION

Hereinafter, the present invention is described in more detail with reference to Examples. However, these Examples are for illustrative purposes only, and the invention is not intended to be limited by these Examples.

Example 1: Cell Isolation

Peripheral venous blood samples newly collected from healthy individuals and cancer patients were treated with heparin and peripheral-blood mononuclear cells (PBMCs) were isolated by Ficoll-paque gradient centrifugation (GE Healthcare, Piscataway, N.J.) The isolated PBMCs were resuspended in RPMI 1640 medium containing 1% FBS for 2 days. Subsequently, naive $CD4^+$ T cell subsets were collected through positive selection using anti-$CD4^+$ antibodies (Miltenyi Biotec, Gladbach, Germany) The purity of the selected $CD4^+$ T cell fractions was approximately 97%.

In order to obtain high purity of $CD4^+CD25^{high}/-$ T cells, the isolated $CD4^+$ T cells were stimulated with 0.1 µg/ml anti-CD3 antibodies (HIT3a; BD PharMingen, San Diego, Calif.) for 7 days, and 100 U/ml IL-2 (Interleukin-2; PeproTech, Rocky Hill, N.J.) was added every 2 days. Subsequently, the cultured $CD4^+$ T cells were stained with the PE-cy5-conjugated anti-CD25 antibody and FITC-conjugated anti-CD4 antibody. Finally, the $CD4^+CD25^{high}$ T cells or $CD4^+CD25^-$ T cells were isolated by using FACS Aria (BD Biosciences, San Jose, Calif.).

Example 2: Antibodies and Flow Cytometry

In the flow cytometry experiment, the present inventors used fluorochrome-conjugated antibodies against CD4, CDS, CD11c, IFN-γ, Foxp3, CTLA-4, CD62L, CD45RO, CD45RA (BD Bioscience), CD19, CD56, CD14, CD127, IL-4, IL-17A, GATA-3, T-bet, RORγt (ebioscience, San Diego, Calif.), and BDCA-2 (Miltenyi Biotec). Also, for anti-AITR antibody, biotinylated AITR-specific antibodies (A27, A35, A41, B32, and B62 clones) were used. Intracellular level of cytokines was measured after 5 hour-long pre-incubation with 50 ng/ml phorbol 12-myristate 13-acetate (PMA), 10 µg/ml ionomycin, and 10 µg/ml Brefeldin A (Sigma-Aldrich, St Louis. Mo.). FACSCalibur flow cytometer (BD Bioscience) was used for all of the flow cytometry analysis and WinMDI software (Ver. 2.9, Scripps. Institute) was used for data analysis.

Example 3: Preparation of Soluble AITR and AITR-Overexpressing Cell

Specific binding of human anti-AITR mAbs was measured by using Enzyme-linked immunosorbent assay (ELISA) or FACS. In order to generate a fusion protein of a water-soluble AITR-ECD (26th to 139th amino acids) and GST protein, a GST-tagged AITR-ECD expression vector (pGEX-6p-1/AITR-ECD) was constructed. First, AITR-coding sequence was amplified by PCR using a sense primer and antisense primer shown in Table 1 and using eDNA extracted from the activated $CD4^+$ T cells as a PCR template. Then the amplified AITR-coding sequence was restriction digested with BamHI/Xhoi, and cloned into a vector pGEX-6p-1 to generate a GST-tagged AITR-ECD expression vector (pGEX-6p-1/AITR-ECD).

TABLE 1

| | Sequence(5' .3') | SEQ ID No. |
|---|---|---|
| Forward Primer | AAGCTTGGTCAGCGCCCCACCGGG | 49 |
| Reverse Primer | CCGGCAGAGCCGCCTTAACTCGAG | 50 |

The pGEX-6p-1/AITR-ECD was transformed into E. coli (BL21-DE3-pLyss) and the protein expression was induced by adding 0.20 mM IPTG. The recombinant AITR-GST proteins expressed in E. coli were purified by running them through a glutathione agarose 4B bead column.

For generating AITR-overexpressing cells, the gene fragment encoding AITR-transmembrane domain (TM)-ECD was inserted in-frame with CD5L sequence in a mammalian vector pcDNA3.1($^+$), i.e. pcDNA3.1($^+$)/CD5L-AITR-TM-ECD. Then pcDNA3.1($^+$)/Empty vector or pcDNA3.1($^+$)/CD5L-AITR-TM-ECD vector was transient transfected into Jurkat cells by electoporation. AITR expression on cell surface was detected by staining with biotin-conjugated anti-AITR mAb.

Example 4: Preparation of Anti-AITR Monoclonal Antibodies (Anti-AITR mAbs)

The pCANTAB5E phagemid vector comprising human Fab antibody eDNA library was transformed into TG1 E. coli cells. Subsequently, the transformants were cultured in 2×YT broth containing 100 µg/ml ampicillin and 50 µg/ml kanamycin, and then superinfected with M13K07 helper phage. After culturing the cells at 30° C. for 24 hours, the cell culture was centrifuged down to collect culture supernatant only. Then the supernatant was added with 3.3% (w/w) polyethylene glycol (Sigma) and 2.3% (w/w) NaCl to precipitate recombinant phage particles obtained. The precipitated phage particles were resuspended in 2×YT broth.

Biopanning was performed using the above-prepared suspension as a library in order to select the phage specific to a human AITR-GST fusion protein by phage display (1 to 4 times biopanning). Among the recombinant phage particles from the culture supernatant of each clone, a positive clone of human AITR-GST fusion protein was selected through ELISA.

In addition, to generate a bivalent form of antibody, Fab genes (VH and V1) obtained from phage displaying were prepared by PCR, and then cloned into a restriction enzyme site of the expression vector pDCMV-DHFR. As a result, an antibody gene and construct thereof of five different clones (A27, A35, A41, B32, and B62) were obtained. To generate a bivalent form of anti-human AITR mAbs, the construct of antibody gene was transiently transfected into HEK293 and CHO cells, and the protein products were purified from the culture supernatant by using a protein G column (GE Healthcare)

Example 5: Epitope Mapping of Anti-AITR Monoclonal Antibodies (Anti-AITR mAbs)

F or identifying a precise epitope recognized by the anti-AITR mAbs of the present invention, twelve different fragments (R1 to R12) corresponding to AITR-ECD were prepared and cloned into a GST-vector, pGEX-6p-1 (FIG. 3A).

The pGEX-6p-1/R1-R12 was transformed into E. coli cell line, BL21-DE3-pLyss, and the protein expression was induced by adding 0.20 mM IPTG. The recombinant R1-GST to R12-GST fusion proteins expressed in E. coli were purified by running them through a glutathione agarose 4B bead column (Peptron). At this time, horseradish peroxidase-coupled anti-human IgG was diluted 10,000 times (Sigma Aldrich, St Louis, Mo., USA) Also, chemiluminescence was monitored by using SuperSignal West Pico Chemiluminescence Substrate (Pierce, Rockford, Ill.).

Example 6: Cell Division and Cytokine Analysis

In the present invention, $CD4^+$ T cells were labeled with CFSE (Molecular Probes, Invitrogen). The proliferation of CFSE-labeled $CD4^+$ T cells ($5 \times 10^5$ cells/well) was stimulated by treating the cells with anti-CD3 antibody (0.1 µg/ml)/IL-2 (100 U/ml) and 5 µg/ml anti-AITR mAb for 72 hr. After 72 hours of culturing, the cell-free supernatant was separated and analyzed for cytokine level by using TH2/T$_h$2 cytokines bead array kit (BD Bioscience), human TGF-β1 Quantikine ELISA kit (R&D system, Minneapolis, Minn.), and human IL-17A ELISA kit (Abcam, Cambridge, UK).

Example 7: Analysis of Differentiated Effector in CD4+ T Cell

Purified CD4+ T cells (5×10$^5$ cells/well) were stimulated with 0.1 µg/ml anti-CD3 antibody and 100 U/ml IL-2 for 3 days. Then, the cultured cells were treated with 5 µg/ml anti-AITR mAbs or 0.1 µg/ml AITR ligand (AITRL) for another 7 days.

Subsequently, the differentiated effector T cell subsets were washed with 1×PBS, and then cultured with a fresh medium containing 5 µg/ml anti-AITR antibody recognizing different epitope for another 7 days while adding 100 U/ml IL-2 for every 2 days. Then the cultured cells were harvested and endogenous IFN-γ, IL-4 and IL-17A were stained for three-color flow cytometry analysis.

Example 8: Analysis of Interaction Between AITR and TRAFs

Purified CD4+ T cells (5×10$^5$ cells/well) were stimulated with 0.1 µg/ml anti-CD3 antibody and 100 U/ml IL-2 for 2 days. The cultured cells were treated with 5 µg/ml anti-AITR mAbs for 24 hr. Then the cells were lysed with 100 pl RIPA buffer (50 mM Tris-HCl (pH 7.4), 150 mM NaCl, 1% Nonidet P-40, 0.25% Na-deoxycholate, 1 mM PMSF, protease inhibitors, and phosphatase inhibitors).

For immunoprecipitation, cell lysates were incubated with 20 pl of 1:1 slurry of protein G-sepharose for 1 hour. Then, the precipitate was washed with 1×PBS, and protein complexes were eluted. Western blot analysis of eluate was performed by using anti-TRAFs (TRAF1, TRAF2, TRAF3, TRAF5, and TRAF6) (Santa Cruz Biotechnology, Santa Cruz, Calif.) or anti-AITR mAbs and using horseradish peroxidase-conjugated goat anti-rabbit IgG or anti-human IgG as a secondary antibody.

In a separate experiment, the sorted CD4+CD25high T cells (5×10$^5$ cells/well) were stimulated with 5 µg/ml anti-AITR mAbs for 24 hr and the interaction between AITR and TRAF was analyzed by using the same method described above.

Example 9: Analysis of Phosphorylation of Endogenous Signaling Pathway Protein Purified CD4+ T cells (1×10$^6$ cells/well) were stimulated with anti-CD3 antibody and IL-2 for 3 days. The cultured cells were treated with anti-AITR mAbs for 2, 6, 12 and 24 hours. Then the cells were harvested and the suspension thereof was prepared. Levels of phospho-STATs (STAT1, STAT2, STAT3, STAT4, STAT5, and STAT6) and master transcription factors (T-bet, GATA-3, RORγt and Foxp3) were analyzed by flow cytometry. The cells in the culture were lysed with RIPA buffer. Subsequently, total protein extract was resolved on 8% to 12% SDS-polyacrylamide gel electrophoresis and immunoblotted with antibodies against NFAT1/2, p-p38, p-ERK1/2, p-JNK1/2, and p-NF-KB (Cell Signaling, Danvers, Mass., USA). The same blot was re-probed with an anti-β-actin antibody as a control for protein loading.

In a separate experiment, the sorted CD4+CD25$^{high}$ T cells (5×10$^5$ cells/well) were stimulated with 5 µg/ml anti-AITR mAbs and phosphorylation of the proteins involved in intracellular signaling pathway was analyzed by the same method described above.

Example 10: Phenotype Conversion of Human CD4+CD25highFoxp3+ (T$_{reg}$) Cell to different Subset Human T$_{reg}$ cells isolated from healthy subjects and cancer patients were sorted by the method described in Example 1. The cells were stimulated with 5 µg/ml anti-AITR mAbs for 7 days while adding 100 U/ml IL-2 every 2 days. Then the cultured cells were harvested and the expression of AITR, CTLA-4, CD62L, CD127, CD45R0 and CD45RA on cell surface was confirmed. Also, endogenous IFN-γ, IL-4 and IL-17A and master transcription factors were stained and the cells were analyzed by flow cytometry. In addition, culture supernatants were collected and the expression of IFN-γ, IL-4, IL-17A, and TGF-was confirmed.

In a separate experiment, the sorted CD4+CD25– (non-T$_{reg}$) cells (5×10$^6$ cells/well) were stimulated with 5 µg/ml anti-AITR mAbs. Culture cells were stained for endogenous IFN-γ, IL-4 and IL-17A and then analyzed by three-color flow cytometry.

Example 11: Statistical Analysis

All experimental data were analyzed with a statistical program called Prism 5.0 GraphPad (San Diego, Calif.) Student's t-test was performed to determine the statistical significance of the difference between test groups.

Experimental Example 1: Generation of Anti-AITR Monoclonal Antibodies

As described in Example 4, five Fab antibodies against AITR were selected from a human Fab antibody library and named as A27, A35, A41, B32, and B62. The antibody A35 comprises a heavy chain variable region of SEQ ID No.5 and a light chain variable region of SEQ ID No.9, and the antibody B62 comprises a heavy chain variable region of SEQ ID No.15 and a light chain variable region of SEQ ID No.16. The antibody A27 comprises a heavy chain variable region of SEQ ID No.19 and a light chain variable region of SEQ ID No.23, and the antibody B32 comprises a heavy chain variable region of SEQ ID No.29 and a light chain variable region of SEQ ID No.33. The antibody A41 comprises a heavy chain variable region of SEQ ID No.39 and a light chain variable region of SEQ ID No.43.

In addition, anti-AITR genes were generated by grafting V$^H$ and V$^L$ DNA sequences into a human IgG1 backbone. Anti-AITR mAbs A27, A35, A41, B32, and B62, were produced by transient transfection of the antibody constructs into HEK293 cells (FIG. 1A). These antibodies showed similar affinity to AITR in the AITR-overexpressed Jurkat cells (FIG. 1B).

Experimental Example 2: Epitope Mapping of Anti-AITR Monoclonal Antibodies

In this experiment, epitopes recognized by five human anti-AITR mAbs selected in Experimental Example 1 were identified. To confirm the epitope, AITR-GST fusion proteins named as R1 to R12 were used (FIG. 3). Immunoblotting results of R0-GST to R12-GST proteins with anti-AITR mAbs demonstrated that the five antibodies were classified into 3 groups based on their recognition site of AITR, i.e., epitope.

A27 and B32 specifically bound to R1 and R2 sites; A35 and B62 specifically bound to R1 to R4 and R8 to R11; and A41 specifically bound to R1 to R6, R8, and R9 (FIG. 3B). As a result of investigating the epitope sites more precisely, it was confirmed that A27 and B32 specifically recognized the sequence of 56th to 65th amino acids (AA 56-65) of AITR-ECD; A35 and B62 specifically recognized the sequence of 41st to 50$^{th}$ amino acids (AA 41-50) of AITR-ECD; and A41 specifically recognized the sequence of 20th to 30th amino acids (AA 20-30) of AITR-ECD (FIG. 3C and Table 2). The epitope site recognized by A35 and B62 was named as SEQ ID No.2; the epitope site recognized by A27 and B32 was named as SEQ ID No.3; and the epitope site recognized by A41 was named as SEQ ID No.4.

TABLE 2

| Antibody | Epitope | SEQ ID No. |
| --- | --- | --- |
| A35&B62 | ECCSEWDCMC (AA 41-50) | 2 |
| A27&B32 | HCGDPCCTTC (AA 56-65) | 3 |
| A41 | GTDARCCRVHT (AA 20-30) | 4 |

Experimental Example 3: Expression of AITR in Immune Cell

The expression of AITR was up-regulated after stimulation of PBMCs, but when PBMCs were not stimulated, mRNA of AITR was not detected. Also, the expression of AITR was significantly up-regulated after CD3 stimulation in T cells. Furthermore, the expression of AITR was analyzed in T cells, B cells, NK cells, and monocytes by flow cytometry. The results demonstrated that the human anti-AITR mAbs of the present invention mainly recognized AITR in the activated CD4$^+$ T cells which had nearly 40-fold higher expression of AITR. When the antibodies were used in CD8$^+$ T cells, B cells, NK cells, and monocytes, neither of resting nor activated AITR was detected (FIG. 1C).

These results demonstrate that the anti-AITR mAbs of the present invention recognize rapidly up-regulated AITR expression in the activated CD4$^+$ T cell population, through TCR-mediated activated signal.

Experimental Example 4: Co-Stimulation of Cell Division and Cytokine Production in Differentiated CD4$^+$ T Cell Population by AITR Signaling After identifying that AITR is expressed mainly in the activated CD4$^+$ T cells (FIG. 1C), the role of AITR was investigated as a co-stimulatory molecule in proliferation and cytokine secretion.

Figure 5:
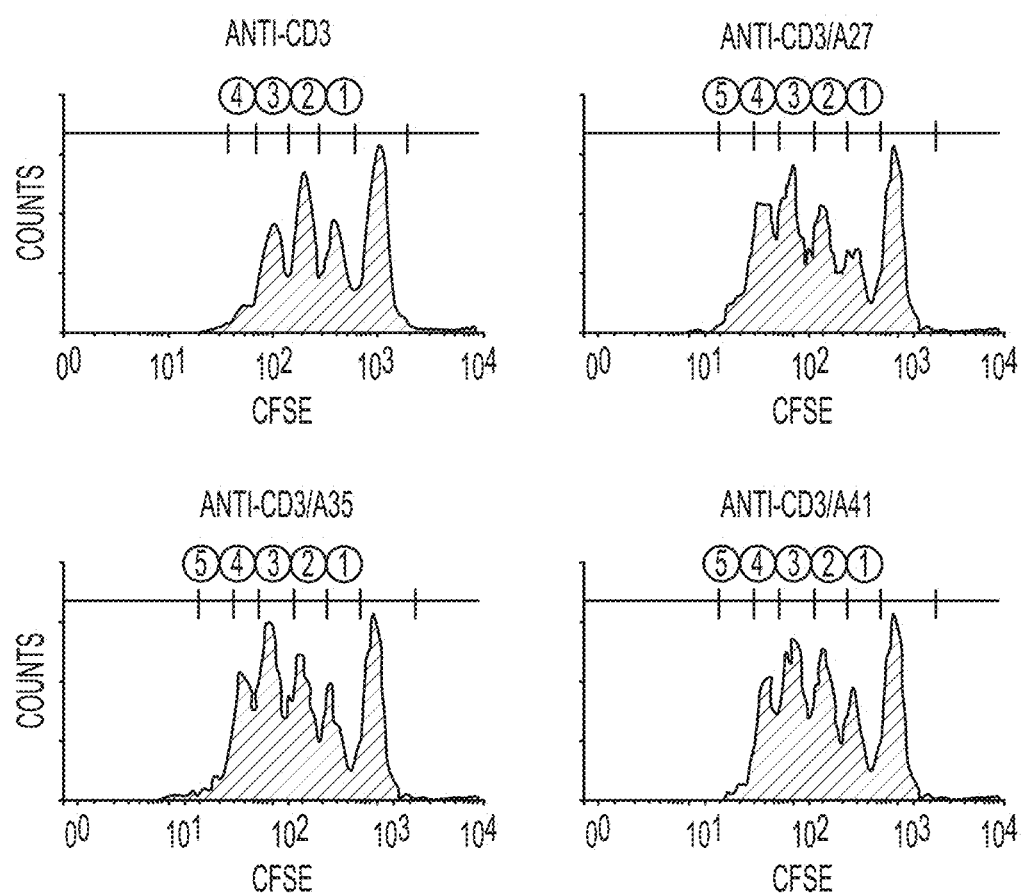
FIG. 5 shows the induction of cell division in CD4+ T cells by anti-AITR mAbs. CFSE-labeled CD4+ T cells were seeded in a flat-bottomed 96-well tissue culture plate coated with anti-CD3/IL-2 and treated with anti-AITR mAbs for 3 days. Histograms are shown in a resolution able to show up to five cycles of cell divisions by flow cytometry. The experimental result shown is based on one of the three independent experiments.

Purified CFSE-labeled CD4$^+$ T cells were stimulated with immobilized anti-CD3 and cultured in the presence of anti-AITR mAbs. Unlike when cultured with anti-CD3 only, when the cells were co-cultured with anti-AITR mAbs and anti-CD3, the proliferation of activated CD4$^+$ T cells was significantly increased (FIG. 5).

Figure 4A:
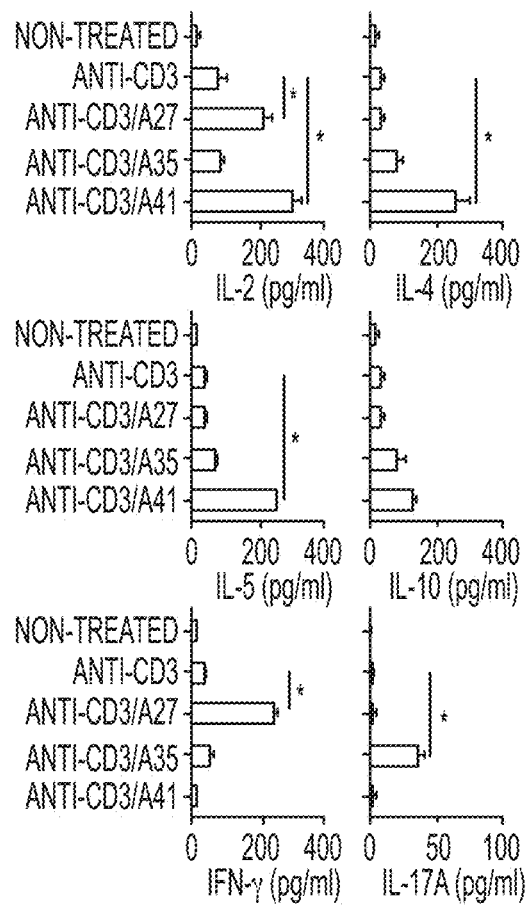
FIG. 4A shows the analysis of cytokine secretion through human $T_H1/T_H2$ cytokine bead array and IL-17A ELISA assay. The purified CD4$^+$ T cells were stimulated with anti-CD3/anti-AITR mAbs (clones A27, A35 or A41) for 3 days.

Subsequently, the culture supernatant was analyzed to identify a type of cytokine secreted depending on the type of anti-AITR mAbs. The results demonstrated that the antibodies of the present invention recognizing different sites of AITR changed the level of different cytokines. To be specific, cell treatment with A27 significantly increased the level of $T_H1$ cytokines IL-2 and IFN-γ, whereas treatment with A35, unlike with A27, increased the level of $T_H17$ cytokine IL-17A. On the other hand, cell treatment with A41 significantly increased the level of $T_H2$ cytokines IL-2, IL-4, and IL-5 (FIG. 4A).

Figure 4B:
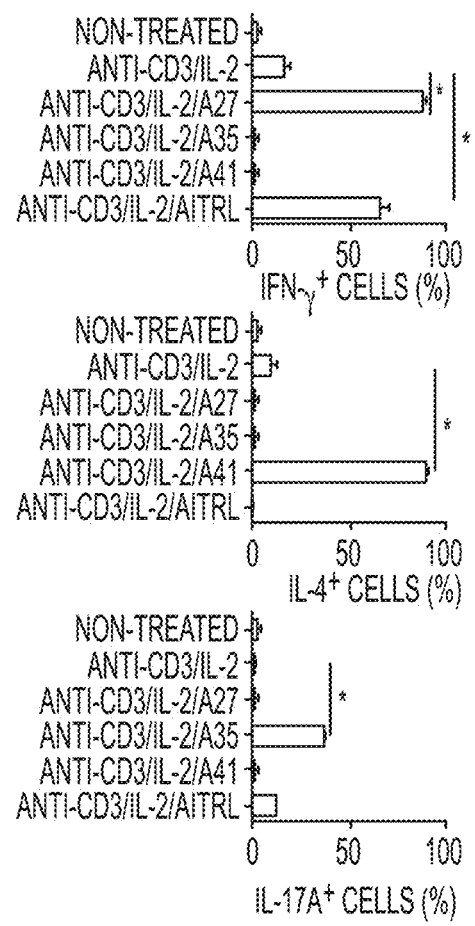
FIG. 4B shows the proportions of cytokine-secreting cells, i.e., IL-4$^+$, IFN-γ, and IL-17A$^+$ cells (%). Purified CD4+ T cells were stimulated with anti-CD3/IL-2 for 3 days and treated with anti-AITR mAb or AITR ligand for additional 7 days. The cultured cells were stained for endogenous IL-4, IFN-γ, and IL-17A, which were then analyzed by flow cytometry. Then the proportion of IL-4+, IFN-γ+, and IL-17A+ cells (%) were calculated. The bar graphs (mean±SD) show the average value of data from three independent experiments, single asterisk, *p<0.05. Together, FIG. 4A and FIG. 4B demonstrate the induction of differentiation of CD4+ T cells into different phenotypes by anti-AITR mAbs which recognize different fragments of AITR-ECDs of the present invention.

In addition, the markers of phenotypic CD4$^+$ T cells for the expression of IFN-γ, IL-17A, and IL-4 in the activated CD4$^+$ T cells were analyzed when the CD4$^+$ T cells were treated with the anti-AITR mAbs or AITRL of the present invention. The results show that when treated with A35 of the present invention, the number of IL-17A-producing CD4$^+$ T cells was increased (37.8±0.11%); when treated with a comparative antibody A27, the number of IFN-γ-producing CD4$^+$ T cells was increased (90.2±0.50%); and when treated with a comparative antibody A41, the number of IL-4-producing CD4$^+$ T cells was increased (91.5±6.21%). Furthermore, the ligand thereof, i.e. AITRL promoted the production of IFN-γ in $T_H1$ CD4$^+$ T cells (FIG. 4B).

Taken together, these results demonstrate that anti-AITR mAbs of the present invention can act as a co-stimulatory signal in CD4$^+$ T cells and promote the cell differentiation to a specific $T_H$ cell and cytokine secretion. In particular, these results suggest that the antibody of the present invention can induce different effects depending on the recognition sites of AITR. To be specific, as A35 antibody of the present invention recognizes the epitope of SEQ ID No.2 among many different sites of AITR in CD4$^+$ T cell, it can differentiate the cell to $T_H17$ cell, thereby producing a $T_H17$ cell cytokine, IL-17A, among different cytokines.

Experimental Example 5: Interaction Between AITR-Family Proteins and TRAF-Family Proteins and Downstream Signal Transduction Previous studies have reported that tumor necrosis factor receptor-associated factor (TRAF) proteins are involved in activation of NF-κB and that downstream signaling molecules such as ERK1/2, JNK1/2, and p38 can be activated by TNFR family members. Also, cytoplasmic domain of AITR contains acidic residues that are conserved in mouse or human and are involved in association of AITR with TRAF protein. AITR is known to interact with TRAF1, TRAF2, and TRAF3, but not with TRAF5 and TRAF6 (Kwon B et al., J Biol Chem 274, 6056-6061, 1999; Ha, H et al., Curr Protoc Immunol. Chapter11:Unit11.9D, 2009). Hence, the present inventors investigated the type of TRAF protein that AITR interacts with when AITR is activated by the anti-AITR mAbs of the present invention in the activated CD4$^+$ T cells.

AITR-TRAF complexes were immunoprecipitated with Protein G, from the lysate of activated CD4$^+$ T cell by using anti-AITR mAbs and the immunoprecipitates were immunoblotted with anti-TRAF antibody and anti-AITR mAbs.

The results demonstrate that the antibodies of the present invention recognizing different sites of AITR recruit different types of TRAF protein to AITR (FIG. 7A). Specifically, A35 which recognizes the epitope of SEQ ID No.2 of the present invention recruited TRAF6, whereas a comparative antibody A27 which recognizes the epitope of SEQ ID No.3 of the present invention recruited TRAF1 and TRAF2 to AITR, and a comparative antibody A41 which recognizes the epitope of SEQ ID No.4 recruited TRAF3 and TRAF5 to AITR. These results suggest that depending on the site of AITR recognized by each antibody, different cytoplasmic signaling can be induced. Furthermore, A35 of the present invention that recruits TRAF6 activated p-p38 and p-NF-kB, whereas a comparative antibody A27 that recruits TRAF1 and TRAF2 activated p-JNK1/2 and p-NF-KB. Also, a comparative antibody A41 which recruits TRAF3 and TRAF5 activated p-ERK1/2 (FIGS. 7A, 7B, and 8).

T cells express NFAT1, NFAT2, and NFAT3, and NFAT proteins are essential for producing effector cytokine when TCR is activated in $T_H$ cells. NFAT proteins also play important roles in regulating $T_H$ cell differentiation. For this reason, the present inventors investigated whether NFAT1 or NFAT2 can be activated when CD4$^+$ T cells are treated with anti-AITR mAbs of the present invention. As a result, it was found that A35 of the present invention recognizing the epitope of SEQ ID No.2 and A27 recognizing the epitope of SEQ ID No.3 increased the number of activated NFAT1 in a time-dependent manner. Unlike A27 and A35, a comparative antibody A41 increased the expression of NFAT2, but not NFAT1 (FIG. 7B).

These results suggest that AITR contains a binding domain for TRAFs or adaptor cytoplasmic molecules that can activate downstream signaling. Also, the results demonstrate that depending on the site of AITR recognized by anti-AITR mAbs, different types of TRAF proteins can be recruited, which then activates different cytoplasmic signaling pathways. Moreover, the AITR antibodies specific to the epitope of SEQ ID No.2 of the present invention not only activate specific TRAF proteins, but also show specific NFAT activities. This result suggests that depending on the site of AITR recognized by AITR antibody, different NFAT translocates into the nucleus, which then induces different NFAT-dependent gene expression.

These results support that particularly A35 and B62 of the present invention recognize the epitope of SEQ ID No.2 among many sites of AITR and recruit TRAF6 among many different types of TRAFs, which then induce p-p38- and p-NF-kB-mediated cytoplasmic signaling pathways, thereby converting the cell to the IL-17A-producing cell, wherein IL-17A is a cytokine of $T_H17$ cell.

Experimental Example 6: Transcription Factors and STATs Protein Activated Differentiation of CD4$^+$ T Cells with Anti-AITR mAbs Previous studies have reported that signaling transducer and activation of transcription (STAT) proteins and master transcription factors are essential in fate determination of $T_H$ cell and cytokine production (Hermann-Kleiter, N. & Baier G, Blood. 15, 2989-2997, 2010) Hence, the present inventors investigated the activities of STAT proteins and master transcription factors in the CD4$^+$ T cells activated by anti-AITR mAbs of the present invention.

Figure 7D:
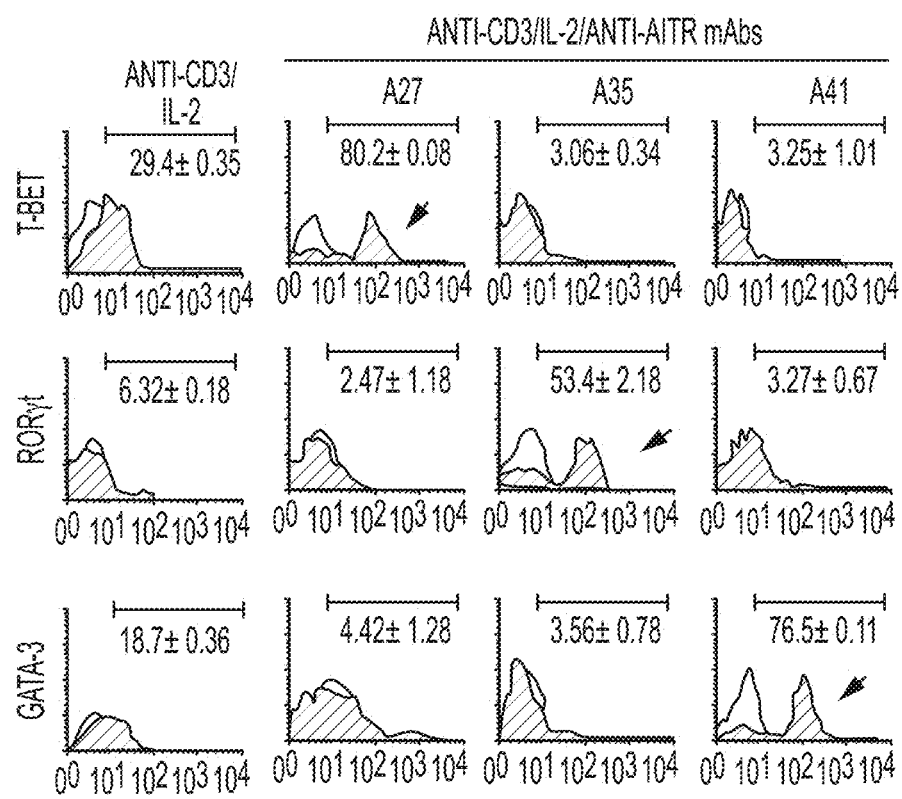
FIG. 7D shows the flow cytometry analysis demonstrating the expression of STAT proteins and master transcription factors. After 24 hr of culturing, the cells were stained with T-bet, GATA-3, or RORγt antibody and analyzed by flow cytometry. Expression of STAT proteins and master transcription factors (filled histograms, arrow pointing) are shown. Numerical values indicated in each panel represent an average of the data (mean±SD) from three independent experiments (compared with control, open histograms). Together, FIG. 7A-D demonstrate that the anti-AITR monoclonal antibodies of the present invention recognizing different ECDs of AITR recruit different signaling proteins in CD4+ T cells, thereby demonstrating different activities. Purified CD4+ T cells were stimulated with anti-CD3/IL-2 for 3 days and were further treated with anti-AITR mAbs for 2, 6, 12, and 24 hr.

A flow cytometric analysis was performed using the antibodies against p-STATs (p-STAT-1, p-STAT-3, p-STAT-4, p-STAT-5, and p-STAT-6) and T-bet, GATA-3, and RORγt. As a result, compared to the group treated with anti-CD4 and IL-2 only without anti-AITR antibody, the group treated with A35 of the present invention showed increased number of activated p-STAT-3 (63.1±1.24%) and RORγt (53.4±2.18%), and the group treated with a comparative antibody A27 showed increased number of activated p-STAT-1 (52.8±0.25%), p-STAT-4 (54.2±0.19%), and T-bet (80.2±0.08%). The group treated with a comparative antibody A41 showed increased number of activated p-STAT-5 (85.1±0.38%), p-STAT-6 (79.2±0.12%), and GATA-3 (76.5±0.11%) (FIGS. 7C, 7D, and 9).

These results suggest that the anti-AITR mAbs of the present invention recognizing different sites of AITR can induce different signaling cascades mediated by AITR in CD4$^+$ T cells. Especially, these results support that A35 and B62 of the present invention recognizing the epitope of SEQ ID No.2 mediate the cell fate determination of $T_H$ cell via a signaling pathway mediated by STAT-3 and RORγt.

Experimental Example 7: Conversion of $T_{reg}$ Cell to $T_H17$ Cell by Anti-AITR mAbs Experimental Examples 5 and 6 showed that the anti-AITR mAbs of the present invention specifically binding to the epitope of SEQ ID No.2 regulate a specific signal transduction factor involved in $T_H$ cell fate determination in CD4$^+$ T cells. That is, according to the epitope sites within AITR, T cell can be converted to a totally different type of $T_H$ cell. Hence, the present inventors hypothesized that by targeting different epitope sites recognized by anti-AITR mAbs of the present invention, functional phenotype of CD4$^+$ T cells can be converted. To confirm this, CD4$^+$ T cells were treated with the representative antibodies A27, A35, and A41 which recognize three different sites of AITR to determine the converting activity thereof.

The results showed that A35 of the present invention converted IFN-γ-producing cells (99.2±0.21%) that were initially induced by A27, a comparative antibody specific to the epitope of SEQ ID No.2, to IL-17A-producing cells (18.8±0.23%). A comparative antibody A41 converted IFN-γ-producing cells (99.2±0.21%) to IL-4-producing cells (38.7±0.32%). In addition, A35-induced IL-17A-producing cells (35.2±0.60%) were converted to IFN-γ-producing cells (82.6±1.21%) by a comparative antibody A27, and converted to IL-4-producing cells (70.5±0.62%) by a comparative antibody A41. A41-induced IL-4-producing cells (98.2±0.29%) were converted to IFN-γ-producing cells (90.1±0.42%) by A27 antibody, and converted to IL-17A-producing cells (16.9±0.58%) by A35 of the present invention (FIGS. 10 and 11).

These results demonstrate that the antibody of the present invention that is specific to the AITR epitope of SEQ ID No.2 can convert the T cell to a specific cytokine-producing cell by recognizing the specific site of AITR, i.e. epitope of SEQ ID No.2 (AA 41-50) Furthermore, these results support that A35 and B62 of the present invention recognizing the epitope of SEQ ID No.2 can convert the T cell specifically to IL-17A-producing $T_H17$ cell, unlike a comparative antibody A27 that induces cell conversion to IFN-γ-producing $T_H1$ cell, and a comparative antibody A41 that induces cell conversion to IL-4-producing $T_H2$ cell.

Experimental Example 8: Converting Activity of Anti-AITR Antibody in CD4$^+$CD25highFoxp3$^+$ ($T_{reg}$) Cell It is known that GITR or AITR acts as a co-stimulatory molecule in $T_{reg}$ cell, and the expression thereof remains high intrinsically in $T_{reg}$ cell even without activation. Hence, the present inventors investigated the role of AITR in $T_{reg}$ cells when stimulated by anti-AITR mAbs. First, after stimulation with anti-CD3 and IL-2, $T_{reg}$ cells (CD4$^+$CD25high cells) and non-$T_{reg}$ cells (CD4$^+$CD25− cells) were isolated from healthy subjects and cancer patients by FACS-sorter. Both of $T_{reg}$ cells isolated from healthy subjects and cancer patients showed constitutive expression of Foxp3 and AITR. Non-$T_{reg}$ cells showed a lower expression of AITR than in $T_{reg}$ cells. The number of $T_{reg}$ cells isolated from cancer patients was three times higher than that from healthy subjects.

Based on the results from the experimental example, it was determined whether the anti-AITR mAbs of the present invention can convert $T_{reg}$ cells. The results showed that A35 of the present invention recognizing the epitope of SEQ ID No.2 converted $T_{reg}$ cells from healthy subjects to IL-17A-producing cells (10.4±0.32%), but could not convert the $T_{reg}$ cells from cancer patients. A comparative antibody A27 recognizing the epitope of SEQ ID No.3 converted the $T_{reg}$ cells from both healthy subjects and cancer patients to IFN-γ-producing cells (93.9±0.12% and 88.2±0.43% respectively). A comparative antibody A41 recognizing the epitope of SEQ ID No.4 of the present invention could not convert the $T_{reg}$ cells isolated from both healthy subjects and cancer patients (FIGS. 12A, 12D, and 13B). In addition, when the secreted cytokines were analyzed, A27 and A35 decreased TGF-secretion, but increased the secretion of IFN-γ and IL-17A respectively. On the other hand, a comparative antibody A41 increased TGF-β secretion in a time-dependent level (FIG. 12B). Furthermore, the mechanisms behind signal transduction were investigated. As a result, it was observed that as shown in Experimental Example 5, A35 of the present invention recruited TRAF6 and activated p-p38 and p-NF-kB signaling pathways. A comparative antibody A27 recruited TRAF1 and TRAF2 and increased the expression of NFAT1, thereby activating p-JNK1/2 and p-NF-kB signaling pathways. These results demonstrate that A27 and A35 reduce the expression of Foxp3 but increase the expression of T-bet or RORγt through the above signaling pathways. Through these mechanisms, A35 of the present invention can convert $T_{reg}$ cell to $T_H17$ cell and a comparative antibody A2 7 can convert $T_{reg}$ cell to $T_H1$ cell (FIGS. 9, 12C, and 15).

However, when $T_{reg}$ cells were treated with A41, it maintained almost the same expression level of Foxp3 in $T_{reg}$ cell (FIGS. 9, 12C, and 15). Thus, it was determined that when A41 recruited TRAF protein to AITR, it recruited TRAF3 more strongly than TRAF5, and activated ERK1/2, NF-kB, and STAT5, thereby inducing different signaling cascade in $T_{reg}$ cell through NFAT1 transcription factor etc (FIGS. 9 and 14).

These results support that the antibody of the present invention recognizing a specific epitope of SEQ ID No.2 can differentiate the cells specifically to $T_H17$ cells through different signaling pathway from those of other epitopes.

Based on the above description, it should be understood by those skilled in the art that various alternatives to the embodiments of the invention described herein may be employed in practicing the invention without departing from the technical idea or essential features of the invention as defined in the following claims. In this regard, the above-described examples are for illustrative purposes only, and the invention is not intended to be limited by these examples. The scope of the present invention should be understood to include all of the modifications or modified form derived from the meaning and scope of the following claims or its equivalent concepts.

The invention claimed is:

1. A method for converting a target T cell to a type 17 helper T ($T_H17$) cell, comprising:
   (a) inducing expression of activation-inducible tumor necrosis factor receptor (AITR) in a target T cell using anti-CD-3/IL-2; and
   (b) treating the target T cell using an antibody comprising
      a heavy chain variable region comprising heavy chain complementarity-determining region 1 (CDR1) represented by SEQ ID NO: 6; heavy chain CDR2 represented by SEQ ID NO: 7; and a heavy chain CDR 3 represented by SEQ ID NO: 8; and
      a light chain variable region comprising light chain CDR1 represented by SEQ ID NO: 10; light chain CDR2 represented by SEQ ID NO: 11; and light chain CDR3 represented by SEQ ID NO: 12,
   thereby converting a target T cell to a type 17 helper T ($T_H17$) cell.

2. The method of claim 1, wherein the target T cell is a type 1 helper T ($T_H1$) cell, a type 2 helper T ($T_H2$) cell, or a regulatory T ($T_{reg}$) cell.

3. The method of claim 1, wherein the antibody comprises an amino acid sequence of a heavy chain variable region represented by SEQ ID NO: 5; and an amino acid sequence of a light chain variable region represented by SEQ ID NO: 9.

4. The method of claim 1, wherein the type 17 helper T ($T_H17$) cell converted by the method increases a level of IL-17A secretion relative to that of the target T cell.

5. The method of claim 1, wherein the target T cell is obtained by removal from a subject having an infectious disease.

6. The method of claim 5, wherein the converted 17 helper T ($T_H17$) cell is administered to the subject having an infectious disease.

7. The method of claim 5, wherein the infectious disease is selected from the group consisting of a viral infection, a fungal infection, a bacterial infection, a protozoan infection, and a parasitic infection.

8. The method of claim 1, wherein the target T cell is obtained by removal from a healthy subject.

9. A method for treating an infectious disease, comprising:
   (a) obtaining a target T cell from a subject having an infectious disease;
   (b) inducing expression of activation-inducible tumor necrosis factor receptor (AITR) in the target T cell using anti-CD-3/IL-2;
   (c) converting the target T cell to a type 17 helper T ($T_H17$) cell by using an antibody comprising
      a heavy chain variable region comprising heavy chain complementarity-determining region 1 (CDR1) represented by SEQ ID NO: 6; heavy chain CDR2 represented by SEQ ID NO: 7; and a heavy chain CDR 3 represented by SEQ ID NO: 8; and
   a light chain variable region comprising light chain CDR1 represented by SEQ ID NO: 10; light chain CDR2 represented by SEQ ID NO: 11; and light chain CDR3 represented by SEQ ID NO: 12; and
   (d) administering the converted type 17 helper T (TH17) cell to the subject having an infectious disease,
   thereby treating an infectious disease.

10. The treating method of claim 9, wherein the target T cell is a type 1 helper T ($T_H1$) cell, a type 2 helper T ($T_H2$) cell, or a regulatory T ($T_{reg}$) cell.

11. The treating method of claim 9, wherein the infectious disease is selected from the group consisting of a viral infection, a fungal infection, a bacterial infection, a protozoan infection, and a parasitic infection.

12. The method of claim 1, wherein AITR expression is induced by stimulating the target T cell with anti-CD3/IL-2 for 2-5 days.

13. The method of claim 1, wherein treating the target T cell comprises incubating with the antibody for 7 days.

14. The method of claim 13, further comprising adding IL-2 to the antibody incubation every 2 days.

15. The method of claim 9, wherein AITR expression is induced by stimulating the target T cell with anti-CD3/IL-2 for 2-5 days.

16. The method of claim 9, wherein converting the target T cell to a type 17 helper T ($T_H17$) cell comprises incubating the target T cell with the antibody of step (c) for 7 days.

17. The method of claim 9, further comprising adding IL-2 to the antibody incubation of step (c) every 2 days.

* * * * *

SEQUENCE LISTING

```
<160> NUMBER OF SEQ ID NOS: 50

<210> SEQ ID NO 1
<211> LENGTH: 139
<212> TYPE: PRT
<213> ORGANISM: Artificial Sequence
<220> FEATURE:
<223> OTHER INFORMATION: Extracellular domain(ECD) of AITR

<400> SEQUENCE: 1

Gly Gln Arg Pro Thr Gly Gly Pro Gly Cys Gly Pro Gly Arg Leu Leu
1               5                   10                  15

Leu Gly Thr Gly Thr Asp Ala Arg Cys Cys Arg Val His Thr Thr Arg
                20                  25                  30

Cys Cys Arg Asp Tyr Pro Gly Glu Glu Cys Cys Ser Glu Trp Asp Cys
            35                  40                  45

Met Cys Val Gln Pro Glu Phe His Cys Gly Asp Pro Cys Cys Thr Thr
        50                  55                  60

Cys Arg His His Pro Cys Pro Pro Gly Gln Gly Val Gln Ser Gln Gly
    65                  70                  75                  80

Lys Phe Ser Phe Gly Phe Gln Cys Ile Asp Cys Ala Ser Gly Thr Phe
                85                  90                  95

Ser Gly Gly His Glu Gly His Cys Lys Pro Trp Thr Asp Cys Thr Gln
                100                 105                 110

Phe Gly Phe Leu Thr Val Phe Pro Gly Asn Lys Thr His Asn Ala Val
            115                 120                 125

Cys Val Pro Gly Ser Pro Pro Ala Glu Pro Pro
        130                 135

<210> SEQ ID NO 2
<211> LENGTH: 10
<212> TYPE: PRT
```

<213> ORGANISM: Artificial Sequence
<220> FEATURE:
<223> OTHER INFORMATION: Epitope of A35 or B62

<400> SEQUENCE: 2

Glu Cys Cys Ser Glu Trp Asp Cys Met Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Epitope of A27 or B32

<400> SEQUENCE: 3

His Cys Gly Asp Pro Cys Cys Thr Thr Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Epitope of A41

<400> SEQUENCE: 4

Gly Thr Asp Ala Arg Cys Cys Arg Val His Thr
1               5                   10

<210> SEQ ID NO 5
<211> LENGTH: 130
<212> TYPE: PRT
<213> ORGANISM: Artificial Sequence
<220> FEATURE:
<223> OTHER INFORMATION: a heavy chain variable region of A35

<400> SEQUENCE: 5

Glu Val Gln Leu Val Gln Ser Gly Gly Gly Leu Val Gln Pro Gly Gly
1               5                   10                  15

Ser Leu Arg Leu Ser Cys Ser Ala Ser Gly Phe Ser Phe Ser Ser Tyr
            20                  25                  30

Ala Met His Trp Val Arg Gln Ala Pro Gly Lys Gly Leu Glu Tyr Val
        35                  40                  45

Ser Gly Ile Ser Asp Asn Gly Gly Ser Thr Lys Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Ser Ser Leu Arg Ser Glu Asp Thr Ala Val Tyr Tyr Cys
                85                  90                  95

Ala Arg Gly Gly Pro Thr Tyr Tyr Asp Phe Trp Ser Gly Tyr Tyr Thr
            100                 105                 110

Asp Glu Asp Ala Phe Asp Ile Trp Gly Gln Gly Thr Leu Val Thr Val
        115                 120                 125

Ser Ser
    130

<210> SEQ ID NO 6
<211> LENGTH: 8
<212> TYPE: PRT
<213> ORGANISM: Artificial Sequence
<220> FEATURE:
<223> OTHER INFORMATION: CDR1 of a heavy chain variable region of A35 or

B62

<400> SEQUENCE: 6

Gly Phe Ser Phe Ser Ser Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: CDR2 of a heavy chain variable region of A35 or
      B62

<400> SEQUENCE: 7

Ile Ser Asp Asn Gly Gly Ser Thr
1               5

<210> SEQ ID NO 8
<211> LENGTH: 23
<212> TYPE: PRT
<213> ORGANISM: Artificial Sequence
<220> FEATURE:
<223> OTHER INFORMATION: CDR3 of a heavy chain variable region of A35 or
      B62

<400> SEQUENCE: 8

Ala Arg Gly Gly Pro Thr Tyr Tyr Asp Phe Trp Ser Gly Tyr Tyr Thr
1               5                   10                  15

Asp Glu Asp Ala Phe Asp Ile
            20

<210> SEQ ID NO 9
<211> LENGTH: 107
<212> TYPE: PRT
<213> ORGANISM: Artificial Sequence
<220> FEATURE:
<223> OTHER INFORMATION: a light chain variable region of A35

<400> SEQUENCE: 9

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Arg Leu Gln Ser Gly Val Pro Ser Arg Phe Ser Gly
    50                  55                  60

Ser Gly Ser Gly Ala Asp Leu Thr Leu Thr Ile Ser Ser Leu Gln Pro
65                  70                  75                  80

Glu Asp Val Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 10
<211> LENGTH: 6
<212> TYPE: PRT
<213> ORGANISM: Artificial Sequence
<220> FEATURE:
<223> OTHER INFORMATION: CDR1 of a light chain variable region of A35 or
      B62

<400> SEQUENCE: 10

Gln Ser Ile Asn Asn Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: CDR2 of a light chain variable region of A35 or
      B62

<400> SEQUENCE: 11

Ala Thr Ser
1

<210> SEQ ID NO 12
<211> LENGTH: 9
<212> TYPE: PRT
<213> ORGANISM: Artificial Sequence
<220> FEATURE:
<223> OTHER INFORMATION: CDR3 of a light chain variable region of A35 or
      B62

<400> SEQUENCE: 12

Gln Gln Ser Tyr Ser Phe Pro Trp Thr
1               5

<210> SEQ ID NO 13
<211> LENGTH: 390
<212> TYPE: DNA
<213> ORGANISM: Artificial Sequence
<220> FEATURE:
<223> OTHER INFORMATION: a heavy chain variable region of A35

<400> SEQUENCE: 13
gaagtgcagc tggtgcagtc tggggggaggc ttggtccagc cggggggggtc cctaagactc      60 tcctgttcag cctctggatt cagcttcagt agtyatgcta tgcactgggt ccgccaggct     120
ccagggaagg gactggaata tgtctcaggt attagtgata tggaggtag cacaaagtac      180 gcagactcag tgaagggcag attcaccatc tccagagaca attcccagaa cacgctgtat     240
cttcaaatga gcagcctgag atctgaggac acggccgtgt attactgtgc gagaggcggg     300
cccacgtatt acgattttg gagtggttat tataccgacg aagatgcttt tgatatctgg      360
ggccaaggca ccctggtcac cgtctcctcg                                       390

<210> SEQ ID NO 14
<211> LENGTH: 321
<212> TYPE: DNA
<213> ORGANISM: Artificial Sequence
<220> FEATURE:
<223> OTHER INFORMATION: a light chain variable region of A35

<400> SEQUENCE: 14
gaaattgtaa tgacacagtc tccatcctcc ctgtctgcat ctgtaggaga cagagtcacc      60
atcacttgcc gggcaagtca gagtattaac aactatttaa actggtatca gcaaaaaccc     120
gggaaagccc ctaagctcct aatctatgct acatccaggt tgcagagtgg cgtcccatcc     180
aggttcagtg gcagtggatc tgggcagat ctcactctca ccatcagcag tctgcaacct      240
gaagatgttg caacttatta ctgtcaacag agctacagtt cccgtggac gttcggccaa      300 gggaccaagg tggagatcaa a                                                321

<210> SEQ ID NO 15
<211> LENGTH: 134
<212> TYPE: PRT
<213> ORGANISM: Artificial Sequence
<220> FEATURE:
<223> OTHER INFORMATION: a heavy chain variable region of B62

<400> SEQUENCE: 15

```
Glu Val Gln Leu Glu Val Gln Leu Val Gln Ser Gly Gly Gly Leu Val
1               5                   10                  15

Gln Pro Gly Gly Ser Leu Arg Leu Ser Cys Ser Ala Ser Gly Phe Ser
            20                  25                  30

Phe Ser Ser Tyr Ala Met His Trp Val Arg Gln Ala Pro Gly Lys Gly
        35                  40                  45

Leu Glu Tyr Val Ser Gly Ile Ser Asp Asn Gly Gly Ser Thr Lys Tyr
    50                  55                  60

Ala Asp Ser Val Lys Gly Arg Phe Thr Ile Ser Arg Asp Asn Ser Gln
65                  70                  75                  80

Asn Thr Leu Tyr Leu Gln Met Ser Ser Leu Arg Ser Glu Asp Thr Ala
                85                  90                  95

Val Tyr Tyr Cys Ala Arg Gly Gly Pro Thr Tyr Tyr Asp Phe Trp Ser
            100                 105                 110

Gly Tyr Tyr Thr Asp Glu Asp Ala Phe Asp Ile Trp Gly Gln Gly Thr
        115                 120                 125

Leu Val Thr Val Ser Ser
    130
```

<210> SEQ ID NO 16
<211> LENGTH: 107
<212> TYPE: PRT
<213> ORGANISM: Artificial Sequence
<220> FEATURE:
<223> OTHER INFORMATION: a light chain variable region of B62

<400> SEQUENCE: 16

```
Glu Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Arg Leu Gln Ser Gly Val Pro Ser Arg Phe Ser Gly
    50                  55                  60

Ser Gly Ser Gly Ala Asp Leu Thr Leu Thr Ile Ser Ser Leu Gln Pro
65                  70                  75                  80

Glu Asp Val Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105
```

<210> SEQ ID NO 17
<211> LENGTH: 402
<212> TYPE: DNA
<213> ORGANISM: Artificial Sequence
<220> FEATURE:
<223> OTHER INFORMATION: a heavy chain variable region of B62

<400> SEQUENCE: 17

```
gaagtgcagc tggaagtgca gctggtgcag tctgggggag gcttggtcca gccgggggg      60
```

```
tccctaagac tctcctgttc agcctctgga ttcagcttca gtagttatgc tatgcactgg    120
gtccgccagg ctccagggaa gggactggaa tatgtctcag gtattagtga taatggaggt    180
agcacaaagt acgcagactc agtgaagggc agattcacca tctccagaga caattcccag    240
aacacgctgt atcttcaaat gagcagcctg agatctgagg acacggccgt gtattactgt    300
gcgagaggcg ggcccacgta ttacgatttt tggagtggtt attataccga cgaagatgct    360
tttgatatct ggggccaagg caccctggtc accgtctcct cg                      402
```

```
<210> SEQ ID NO 18
<211> LENGTH: 321
<212> TYPE: DNA
<213> ORGANISM: Artificial Sequence
<220> FEATURE:
<223> OTHER INFORMATION: a light chain variable region of B62

<400> SEQUENCE: 18
```

```
gaaattgtaa tgacacagtc tccatcctcc ctgtctgcat ctgtaggaga cagagtcacc     60
atcacttgcc gggcaagtca gagtattaac aactatttaa actggtatca gcaaaaaccc    120
gggaaagccc ctaagctcct aatctatgct acatccaggt tgcagagtgg cgtcccatcc    180
aggttcagtg gcagtggatc tgggqcagat ctcactctca ccatcagcag tctgcaacct    240
gaagatgttg caacttatta ctgtcaacag agctacagtt cccgtggac gttcggccaa    300 gggaccaagg tggagatcaa a                                              321
```

```
<210> SEQ ID NO 19
<211> LENGTH: 128
<212> TYPE: PRT
<213> ORGANISM: Artificial Sequence
<220> FEATURE:
<223> OTHER INFORMATION: a heavy chain variable region of A27

<400> SEQUENCE: 19
```

Gln Val Gln Leu Val Gln Ser Gly Thr Gln Val Lys Met Pro Gly Ala
1               5                   10                  15

Ser Val Lys Val Ser Cys Lys Ala Ser Gly Tyr Thr Phe Asp Asp Tyr
            20                  25                  30

Gly Ile Gly Trp Val Arg Gln Ala Pro Gly Gln Gly Leu Glu Trp Met
        35                  40                  45

Gly Trp Ile Ser Pro Tyr Thr His Arg Thr Asn Ser Ser Pro Lys Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Thr Tyr Tyr Asp Phe Trp Ser Gly Tyr Phe Asp Asn
            100                 105                 110

Gly Ala Phe Asp Ile Trp Gly Gln Gly Thr Leu Val Thr Val Ser Ser
        115                 120                 125

```
<210> SEQ ID NO 20
<211> LENGTH: 8
<212> TYPE: PRT
<213> ORGANISM: Artificial Sequence
<220> FEATURE:
<223> OTHER INFORMATION: CDR1 of a heavy chain variable region of A27

<400> SEQUENCE: 20
```

Gly Tyr Thr Phe Asp Asp Tyr Gly

```
<210> SEQ ID NO 21
<211> LENGTH: 8
<212> TYPE: PRT
<213> ORGANISM: Artificial Sequence
<220> FEATURE:
<223> OTHER INFORMATION: CDR2 of a heavy chain variable region of A27

<400> SEQUENCE: 21

Ile Ser Pro Tyr Thr His Arg Thr
1               5

<210> SEQ ID NO 22
<211> LENGTH: 21
<212> TYPE: PRT
<213> ORGANISM: Artificial Sequence
<220> FEATURE:
<223> OTHER INFORMATION: CDR3 of a heavy chain variable region of A27

<400> SEQUENCE: 22

Ala Arg Asp Gly Thr Tyr Tyr Asp Phe Trp Ser Gly Tyr Phe Asp Asn
1               5                   10                  15

Gly Ala Phe Asp Ile
            20

<210> SEQ ID NO 23
<211> LENGTH: 110
<212> TYPE: PRT
<213> ORGANISM: Artificial Sequence
<220> FEATURE:
<223> OTHER INFORMATION: a light chain variable region of A27

<400> SEQUENCE: 23

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Cys Gly Thr Trp Asp Ser Ser Leu
                85                  90                  95

Asn Ala Trp Val Phe Gly Gly Gly Thr Lys Leu Thr Val Leu
            100                 105                 110

<210> SEQ ID NO 24
<211> LENGTH: 8
<212> TYPE: PRT
<213> ORGANISM: Artificial Sequence
<220> FEATURE:
<223> OTHER INFORMATION: CDR1 of a light chain variable region of A27

<400> SEQUENCE: 24

Thr Ser Asn Ile Gly Asn Asn Tyr
1               5

<210> SEQ ID NO 25
<211> LENGTH: 3
<212> TYPE: PRT
```

```
<213> ORGANISM: Artificial Sequence
<220> FEATURE:
<223> OTHER INFORMATION: CDR2 of a light chain variable region of A27

<400> SEQUENCE: 25

Asp Asn Tyr
1

<210> SEQ ID NO 26
<211> LENGTH: 11
<212> TYPE: PRT
<213> ORGANISM: Artificial Sequence
<220> FEATURE:
<223> OTHER INFORMATION: CDR3 of a light chain variable region of A27

<400> SEQUENCE: 26

Gly Thr Trp Asp Ser Ser Leu Asn Ala Trp Val
1               5                   10

<210> SEQ ID NO 27
<211> LENGTH: 384
<212> TYPE: DNA
<213> ORGANISM: Artificial Sequence
<220> FEATURE:
<223> OTHER INFORMATION: a heavy chain variable region of A27

<400> SEQUENCE: 27
caggtccagc tggtgcagtc tggaactcag gtgaagatgc tggggcctca gtgaaggtc        60 tcctgcaagg cttctggtta cacctttgac gactatggta tcggctgggt gcgacaggcc      120
cctggacaag gcttgaatg gatgggatgg atcagcccttt acactcatag acaaattct       180 tcaccgaagc tccaggacag agtcaccatg accacagaca catccacgag cacagcctac      240
atggagctga ggagcctgag atctgacgac acggccgtgt attactgtgc gagagatggg      300
acgtattacg attttggag tggttatttc gacaatggtg cttttgatat ctggggccaa       360
ggcaccctgg tcaccgtctc ctca                                              384

<210> SEQ ID NO 28
<211> LENGTH: 330
<212> TYPE: DNA
<213> ORGANISM: Artificial Sequence
<220> FEATURE:
<223> OTHER INFORMATION: a light chain variable region of A27

<400> SEQUENCE: 28
cagtctgtcg tgacgcagcc gccctcagtg tctgcggccc caggacagaa ggtcaccatc        60
tcctgctctg gaagcacctc caacattggg aataattatg tatcctggta ccagcaactc      120
ccaggaacag cccccaaact cctcatttat gacaattata gcgaccctc tgggattcct       180 gaccgattct ctggctccaa gtctggcacg tcagccaccc tgggcatcac cggactccgg      240
actggggacg aggccgatta tttctgcgga acatgggata gtagcctgaa tgcttgggtg      300
ttcggcgggg ggaccaagct gaccgtccta                                         330

<210> SEQ ID NO 29
<211> LENGTH: 123
<212> TYPE: PRT
<213> ORGANISM: Artificial Sequence
<220> FEATURE:
<223> OTHER INFORMATION: a heavy chain variable region of B32

<400> SEQUENCE: 29

Glu Val Gln Leu Leu Glu Ser Gly Gly Gly Leu Ile Gln Pro Gly Gly
```

```
                1               5                  10                  15
Ser Leu Arg Leu Ser Cys Ala Ala Ser Gly Phe Thr Phe Ser Thr Tyr
        20                  25                  30

Gly Met Ser Trp Val Arg Gln Ala Pro Gly Lys Gly Leu Glu Trp Val
        35                  40                  45

Ser Gly Ile Thr Gly Ser Ala Gly Gly Ser Thr Asn Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Tyr Ser Ser Asn Trp Arg Ser Ala Phe Asp Ile
            100                 105                 110

Trp Gly Gln Gly Thr Met Val Thr Val Ser Ser
        115                 120

<210> SEQ ID NO 30
<211> LENGTH: 8
<212> TYPE: PRT
<213> ORGANISM: Artificial Sequence
<220> FEATURE:
<223> OTHER INFORMATION: CDR1 of a heavy chain variable region of B32

<400> SEQUENCE: 30

Gly Phe Thr Phe Ser Thr Tyr Gly
1               5

<210> SEQ ID NO 31
<211> LENGTH: 10
<212> TYPE: PRT
<213> ORGANISM: Artificial Sequence
<220> FEATURE:
<223> OTHER INFORMATION: CDR2 of a heavy chain variable region of B32

<400> SEQUENCE: 31

Ile Thr Gly Ser Ala Gly Gly Ser Thr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: CDR3 of a heavy chain variable region of B32

<400> SEQUENCE: 32

Ala Lys Gly Tyr Ser Ser Asn Trp Arg Ser Ala Phe Asp Ile
1               5                   10

<210> SEQ ID NO 33
<211> LENGTH: 108
<212> TYPE: PRT
<213> ORGANISM: Artificial Sequence
<220> FEATURE:
<223> OTHER INFORMATION: a light chain variable region of B32

<400> SEQUENCE: 33

Ser Tyr Glu Leu Met Gln Pro Pro Ser Val Ser Val Ser Pro Gly Gln
1               5                   10                  15

Thr Ala Gly Ile Thr Cys Ser Gly Asp Ala Leu Pro Lys Gln Tyr Ala
            20                  25                  30

Tyr Trp Tyr Gln Gln Arg Pro Gly Gln Ala Pro Val Leu Leu Ile Tyr
```

```
                35                  40                  45
Lys Asp Thr Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro Val Phe Gly Gly Gly Thr Lys Leu Thr Val Leu
            100                 105
```

<210> SEQ ID NO 34
<211> LENGTH: 6
<212> TYPE: PRT
<213> ORGANISM: Artificial Sequence
<220> FEATURE:
<223> OTHER INFORMATION: CDR1 of a light chain variable region of B32

<400> SEQUENCE: 34

```
Ala Leu Pro Lys Gln Tyr
1               5
```

<210> SEQ ID NO 35
<211> LENGTH: 3
<212> TYPE: PRT
<213> ORGANISM: Artificial Sequence
<220> FEATURE:
<223> OTHER INFORMATION: CDR2 of a light chain variable region of B32

<400> SEQUENCE: 35

```
Lys Asp Thr
1
```

<210> SEQ ID NO 36
<211> LENGTH: 11
<212> TYPE: PRT
<213> ORGANISM: Artificial Sequence
<220> FEATURE:
<223> OTHER INFORMATION: CDR3 of a light chain variable region of B32

<400> SEQUENCE: 36

```
Gln Ser Ala Asp Ser Ser Gly Thr Tyr Pro Val
1               5                   10
```

<210> SEQ ID NO 37
<211> LENGTH: 369
<212> TYPE: DNA
<213> ORGANISM: Artificial Sequence
<220> FEATURE:
<223> OTHER INFORMATION: a heavy chain variable region of B32

<400> SEQUENCE: 37

```
gaggtccagc tgttggagtc tgggggaggc ttgatacagc ctgggggtc  cctgagactc      60 tcctgtgcag cctctggatt cacatttagc acctacggca tgagctgggt ccgccaggct     120
ccagggaagg ggctggagtg ggtctcaggt attactggta gtgctggtgg tggtagcaca     180
aattacgcag actccgtgaa gggccggttc accatctcca gagacaattc caagaacacg     240
ctgtatctgc aaatgaacag cctgagagcc gaggacacgg ccgtttatta ctgtgcgaag     300
gggtatagca gcaactggcg gtcagctttt gatatctggg gccaagggac aatggtcacc     360
gtctcctca                                                             369
```

<210> SEQ ID NO 38

<211> LENGTH: 324
<212> TYPE: DNA
<213> ORGANISM: Artificial Sequence
<220> FEATURE:
<223> OTHER INFORMATION: a light chain variable region of B32

<400> SEQUENCE: 38

```
tcctatgagc tgatgcagcc accctcggtg tcagtgtccc caggacagac ggccgggatc    60
acctgctctg gagatgcatt gccaaagcaa tatgcttatt ggtaccagca gaggccaggc   120
caggcccctg tgttgctcat atataaagac actgagaggc cctcagggat ccctgagcga   180
ttctctggct ccagctcagg gacaacagtc acgttgacca tcagtggagt ccaggcagaa   240
gacgaggctg actattactg tcaatcagca gacagcagtg gtacttatcc ggtgttcggc   300
ggagggacca agctgaccgt ccta                                          324
```

<210> SEQ ID NO 39
<211> LENGTH: 127
<212> TYPE: PRT
<213> ORGANISM: Artificial Sequence
<220> FEATURE:
<223> OTHER INFORMATION: a heavy chain variable region of A41

<400> SEQUENCE: 39

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ala Ala Ala Gly Pro Pro Tyr Tyr Tyr Tyr Tyr Tyr
            100                 105                 110

Tyr Met Asp Val Trp Gly Lys Gly Thr Thr Val Thr Val Ser Ser
        115                 120                 125
```

<210> SEQ ID NO 40
<211> LENGTH: 8
<212> TYPE: PRT
<213> ORGANISM: Artificial Sequence
<220> FEATURE:
<223> OTHER INFORMATION: CDR1 of a heavy chain variable region of A41

<400> SEQUENCE: 40

```
Gly Phe Thr Phe Ser Ser Tyr Ala
1               5
```

<210> SEQ ID NO 41
<211> LENGTH: 8
<212> TYPE: PRT
<213> ORGANISM: Artificial Sequence
<220> FEATURE:
<223> OTHER INFORMATION: CDR2 of a heavy chain variable region of A41

<400> SEQUENCE: 41

```
Ile Ser Tyr Asp Gly Ser Asn Lys
1               5
```

```
<210> SEQ ID NO 42
<211> LENGTH: 20
<212> TYPE: PRT
<213> ORGANISM: Artificial Sequence
<220> FEATURE:
<223> OTHER INFORMATION: CDR3 of a heavy chain variable region of A41

<400> SEQUENCE: 42

Ala Arg Gly Ile Ala Ala Ala Gly Pro Pro Tyr Tyr Tyr Tyr Tyr
1               5                   10                  15

Tyr Met Asp Val
            20

<210> SEQ ID NO 43
<211> LENGTH: 107
<212> TYPE: PRT
<213> ORGANISM: Artificial Sequence
<220> FEATURE:
<223> OTHER INFORMATION: a light chain variable region of A41

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Tyr Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Gly Gly
    50                  55                  60

Arg Gly Tyr Gly Thr Asp Phe Thr Leu Thr Ile Asn Ser Leu Gln Pro
65                  70                  75                  80

Glu Asp Phe Ala Thr Tyr Phe Cys Gln Gln Ser Tyr Thr Ser Pro Leu
                85                  90                  95

Thr Phe Gly Gln Gly Thr Lys Val Asp Ile Lys
            100                 105

<210> SEQ ID NO 44
<211> LENGTH: 6
<212> TYPE: PRT
<213> ORGANISM: Artificial Sequence
<220> FEATURE:
<223> OTHER INFORMATION: CDR1 of a light chain variable region of A41

<400> SEQUENCE: 44

Gln Thr Ile Tyr Asn Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: CDR2 of a light chain variable region of A41

<400> SEQUENCE: 45

Ala Ala Ser
1

<210> SEQ ID NO 46
<211> LENGTH: 9
<212> TYPE: PRT
<213> ORGANISM: Artificial Sequence
```

```
<220> FEATURE:
<223> OTHER INFORMATION: CDR3 of a light chain variable region of A41

<400> SEQUENCE: 46

Gln Gln Ser Tyr Thr Ser Pro Leu Thr
1               5

<210> SEQ ID NO 47
<211> LENGTH: 381
<212> TYPE: DNA
<213> ORGANISM: Artificial Sequence
<220> FEATURE:
<223> OTHER INFORMATION: a heavy chain variable region of A41

<400> SEQUENCE: 47
caggtccagc tggtggagtc tgggggaggc gtggtccagc ctgggaggtc cctgagactc      60
tcctgtgcag cctctggatt caccttcagt agctatgcta tgcactgggt ccgccaggct     120
ccaggcaagg gctgagtg gtggcagtt atatcatatg atggaagtaa taaatactac        180
gcagactccg tgaagggccg attcaccatc tccagagaca attccaagaa cacgctgtat     240
ctgcaaatga acagcctgag agctgaggac acggctgtgt attactgtgc gagaggaata     300
gcagcagctg gcccccccta ctactactac tactactaca tggacgtctg ggcaaaggg      360 accacggtca ccgtctcctc a                                              381

<210> SEQ ID NO 48
<211> LENGTH: 321
<212> TYPE: DNA
<213> ORGANISM: Artificial Sequence
<220> FEATURE:
<223> OTHER INFORMATION: a light chain variable region of A41

<400> SEQUENCE: 48
gacatccaga tgacccagtc tccatcctcc ctgtctgctt ctgtaggaga cagagtcacc      60
atcacttgcc gggcaagtca gaccatttac aactatctaa attggtatca gcagaagcca     120
gggaaagccc ctaagctcct gatctatgct gcatccagtt tgcaaagtgg ggtcccatca     180
aggttcggtg ccgtggata tgggacagat ttcactctca ccatcaacag tctgcaacct      240
gaagattttg caacttactt ctgtcaacag agttacacga gtcctctcac ttttggccag     300
gggaccaaag tggatatcaa a                                              321

<210> SEQ ID NO 49
<211> LENGTH: 24
<212> TYPE: DNA
<213> ORGANISM: Artificial Sequence
<220> FEATURE:
<223> OTHER INFORMATION: forward primer

<400> SEQUENCE: 49
aagcttggtc agcgccccac cggg                                            24

<210> SEQ ID NO 50
<211> LENGTH: 24
<212> TYPE: DNA
<213> ORGANISM: Artificial Sequence
<220> FEATURE:
<223> OTHER INFORMATION: reverse primer

<400> SEQUENCE: 50
ccggcagagc cgccttaact cgag                                            24
```